(12) United States Patent
Qi et al.

(10) Patent No.: US 6,329,989 B1
(45) Date of Patent: *Dec. 11, 2001

(54) OCULAR OPTICAL SYSTEM SIMULATING METHOD AND SIMULATING APPARATUS

(75) Inventors: Hua Qi; Ikuka Tanaka, both of Tokyo (JP)

(73) Assignee: Hoya Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 4 days.

(21) Appl. No.: 09/415,498

(22) Filed: Oct. 12, 1999

(30) Foreign Application Priority Data

Oct. 9, 1998 (JP) .................................................. 10-288077

(51) Int. Cl.[7] ...................................................... G06T 17/00

(52) U.S. Cl. .............................................................. 345/428

(58) Field of Search ...................................... 345/428, 429, 345/430, 139; 359/374, 407, 480, 618, 364, 725; 434/38, 43; 623/4.1, 6.63, 6.64

(56) References Cited

U.S. PATENT DOCUMENTS

| | | | |
|---|---|---|---|
| 4,045,116 | * 8/1977 | La Russa | 359/364 |
| 4,645,459 | * 2/1987 | Graf et al. | 434/43 |
| 5,532,770 | 7/1996 | Schmeoder et al. | |
| 5,546,142 | 8/1996 | Kobayashi. | |
| 5,982,549 | * 11/1999 | Kubala et al. | 359/618 |

FOREIGN PATENT DOCUMENTS

| | | |
|---|---|---|
| 0 734 683 | 10/1996 | (EP). |
| 0 734 683 A2 | 10/1996 | (EP). |
| 0 810 427 A1 | 12/1997 | (EP). |

OTHER PUBLICATIONS

Systems & Computer in Japan, US, Scripta Technica Journals, NY, vol. 26, No. 1, Jan. 1, 1995, pp. 62–72, "Restoration of Shift Variant Blurred Image Estimating the Parameter . . .", Hashimoto et al., XP000526355.

IEEE Transactions on Image Processing, US, IEEE Inc., NY, vol. 2, No. 2, Apr. 1, 1993, pp. 141–151, XP000380854, "Blur Identification By Residual Spectral Matching", A. E. Savakis et al.

(List continued on next page.)

*Primary Examiner*—George Manuel
(74) *Attorney, Agent, or Firm*—Griffin & Szipl, P.

(57) ABSTRACT

There are provided an ocular optical system simulating method and a simulating apparatus which enable simulation of how things can be seen, together with fluctuation, deformation, blur, etc., occurring when a lens system such as a progressive addition lens is worn. A rotation-based retinal image, defined as an image obtained by turning an eye-ball with respect to all object points within a field of vision and by connecting images caught at the fovea, is made. The image is made by first creating an original image having a specific angular field of vision and entering the eye having a specific rotation center point. Then, a deformed original image having deformation occurring when the original image is seen through the lens system is created by using ray tracing. A PSF on the retina of an eye-model from light from the object points of the original image in an optical system composed of the lens system and a spectacle model is determined. Next, the deformed original image and the PSF of each pixel of the original image are convoluted. The obtained rotation-based retinal image is edited further to result in a motion picture image of the rotation-based retinal image. The PSF is found by selecting sampling points on an object and the PSF other than those at the sampling points is found by using approximation methods including spline interpolation.

42 Claims, 22 Drawing Sheets

(7 of 22 Drawing Sheet(s) Filed in Color)

OTHER PUBLICATIONS

Applied Optics, US, Optical Society of America, Wasington, vol. 35, No. 35, Dec. 10, 1996, pp. 6896–6908, "Reconfiguration Lens with 1–32 an Electro–Optical Learning System", Y. Takaki et al., XP000640867.

Computer Graphics Proceedings (Siggraph), US, NY, IEEE, 1995, pp. 325–334, XP000546244, "Physically–Based Glare Effects For Digital Images", G. Spencer et al.

IEEE Tranasactions on the Processing, US, IEEE Inc., NY, vol. 2, No. 2, Apr. 1, 1993 pp. 252–259, "On The Accuracy of PSF Representation in Image Restoration", A. E. Savakis et al., XP000380863.

\* cited by examiner $$\tan \beta = \frac{y}{x}, \tan \gamma = \frac{z}{x}$$

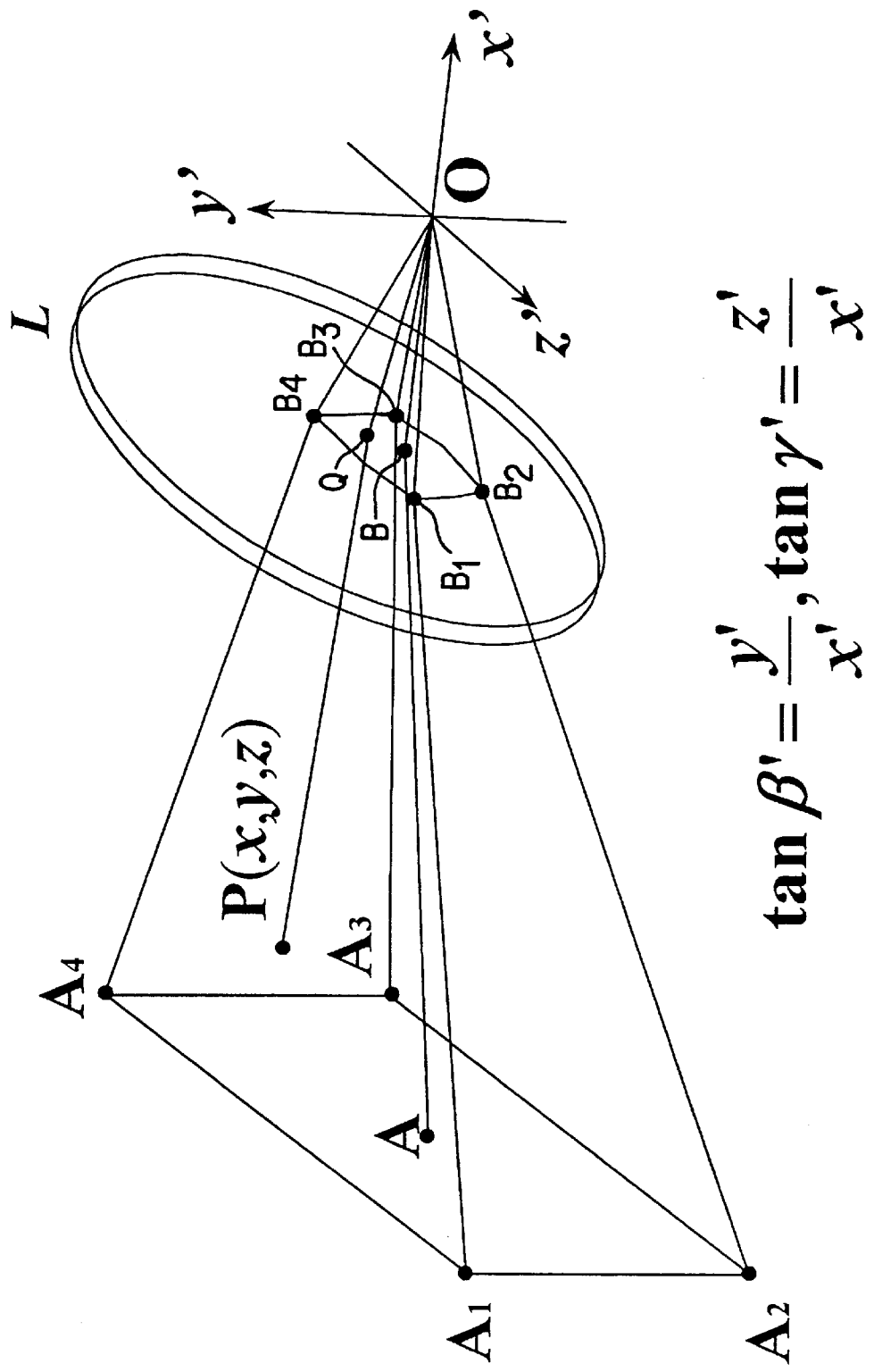

OPTICAL PARAMETERS OF NAVARRO'S EYE SIMULATION (NON-CCOMMODATED)

| Radius of Curvature (mm) | |
|---|---|
| Front surface of cornea | 7.72 |
| Rear surface of cornea | 62 |
| Front surface of crystalline lens | 10.2 |
| Rear surface of crystalline lens | −6.0 |
| Asphericity Q | |
| Front surface of cornea | −0.26 |
| Front surface of crystalline lens | −3.1316 |
| Rear surface of crystalline lens | −1.0 |
| Thickness (mm) | |
| Cornea | 0.55 |
| Anterior sac | 3.05 |
| Crystalline lens | 4.0 |
| Vitreous humor | 16.4 |
| Refractive Index | |
| Cornea | 1.367 |
| Anterior sac | 1.3374 |
| Crystalline lens | 1.42 |
| Vitreous humor | 1.336 |
| Refracting Power (D) | |
| | 60.4 |

FIG.4

EQUATION OF DEPENDENCE ON ACCOMMODATION POWER OF PARAMETERS

| Lens parameter | Equation of Dependence on Accommodation Power (A) |
|---|---|
| Radius of curvature of front face of crystalline lens | $R_3(A) = 10.2000 - 7.7500 \ln(A+1)$ |
| Asphericity of rear face of crystalline lens | $Q_3(A) = -3.1316 + 0.3400 \ln(A+1)$ |
| Radius of curvature of front face of crystalline lens | $R_4(A) = -6.0000 + 0.2294 \ln(A+1)$ |
| Asphericity of rear face of crystalline lens | $Q_4(A) = -1.0000 - 0.1230 \ln(A+1)$ |
| Thickness of anterior sac | $D_2(A) = 3.0500 - 0.0500 \ln(A+1)$ |
| Thickness of crystalline lens | $D_3(A) = 4.0000 + 0.1000 \ln(A+1)$ |
| Refractive index of crystalline lens | $n_3(A) = 1.4200 + 9.00 \times 10^{-5}(10.00A + A^2)$ |

FIG.5

AN OUTSIDE SCENE THROUGH PAL    FIG.11

AN INDOOR SCENE THROUGH THE DISTANCE VISION AREA OF PAL

AN INDOOR SCENE THROUGH THE NEAR VISION AREA OF PAL   FIG. 13

A SCENE OF READING THROUGH THE NEAR VISION AREA OF PAL

OCULAR OPTICAL SYSTEM SIMULATING METHOD AND SIMULATING APPARATUS

BACKGROUND OF THE INVENTION (a) Field of the Invention

The invention relates to an ocular optical system simulating method and a simulating apparatus for simulating how things are seen when the outside world is observed through a lens system placed in front of the eyes.

(b) Related Art

An apparatus has been described in Japanese Patent Laid-Open No. Hei. 8-266473 applied for previously by the assignee of the present application. In this prior application, there are described an ocular optical system simulating method and a simulating apparatus for simulating how things are seen when the outside world is observed through a lens system placed in front of eyes.

The apparatus described in the above-mentioned publication simulates an image of scenery in a scope which can be visualized by turning eyes while wearing spectacle lenses, by computations including computing the Point Spread Function (PSF). The disclosed apparatus and method have enabled simulation of the sight of scenery in a wide angle involving rotation of human eyes while wearing optical lenses such as spectacle lenses.

Unpleasant sensations of fluctuation, deformation and blur in wearing progressive addition lenses (PAL) are obtained in certain cases, even though these lenses fulfill the function of accommodating far and near distances. Therefore, suppression of these unpleasant sensations to the greatest degree possible while accommodating for the far and near is desirable in designing a progressive addition lens. To this end, it is most desirable for a designer himself to know whether the designed lens is accompanied by unpleasant fluctuation, deformation and blur. The above-mentioned conventional ocular optical system simulating method is very useful for certain purposes because it can simulate scenery in a wide angle involving the rotation of human eyes in wearing optical lenses such as spectacles. However, the above system cannot simulate the deformation, blur, etc., which the wearer may feel in reality by also taking human perception into consideration. Therefore, these methods have not always been sufficient to fulfill the purpose of allowing the designer himself to know in advance what kind of deformation and blur the wearer actually perceives when the wearer wears the designed lenses. Still more, this system cannot deal at all with the fluctuation, which is considered to be the most serious problem in actually wearing lenses.

An image of the outside world perceived by a human through the eyes is not considered to be an optical image formed on the retina of the eye in accordance with optical principles. That is, the distribution density of photoreceptors on the retina is high around the fovea and is low at peripheral parts. Accordingly, if a strictly optical image formed on the retina is perceived, it must be perceived as an image which is clear only around the center and is unclear at the periphery even when the optical image is ideally formed. However, one can sense that one can see clearly anywhere within a field of vision as long as one has healthy eyes. This is because the operation of perception is not a simple operation of detecting the optical image projected on the retina as it is, but is based on the result of a complex system of processing neural information on and after the retina.

According to the research of the inventors, although such perception may not be simulated directly, it has become clear that the result of the perception may be reproduced approximately by image processing based on certain assumptions found by the inventors.

The present invention has been devised based on the background described above and its object is to provide an ocular optical system simulating method and a simulating apparatus which enables simulation of how things are seen, with fluctuation, deformation, blur and the like, while wearing a lens system such as a progressive addition lens.

SUMMARY OF THE INVENTION

In accordance with the above objects, the present invention provides a method for simulating how things are seen through a lens system placed in front of the eye whose center of rotation is placed at a specific position and whose central visual line is directed to a specific direction, comprising the steps of:

(1) Creating an original image within a field of view centered with said central visual line; (2) Creating a deformed original image to approximate deformation occurring when the original image is seen through said lens system;(3) Determining point spread functions (PSF), defined as the distribution of luminance on the retina originated from the corresponded object point, for each object point within the original image;(4) Convoluting the deformed original image with the point spread functions to create a rotation-based retinal image.

In yet another preferred embodiment, the invention provides an apparatus for simulating an apparatus for simulating how things are seen through a lens system placed in front of the eye whose center of rotation is placed at a specific position and whose central visual line is directed to a specific direction comprising: (1) Means for creating an original image within a field of view centered with said central visual line; (2) Means for creating a deformed original image to approximate deformation occurring when the original image is seen through said lens system; (3) Means for determining point spread functions (PSF), defined as the distribution of luminance on the retina originated from the corresponded object point, for each object point within the original image; (4) Means for convoluting the deformed original image with the point spread functions to create a rotation-based retinal image; (5) Means for displaying the rotation based optical image.

As means for solving the above-mentioned problems, one further embodiment of invention provides an ocular optical system simulating method for simulating how things are seen when the outside world is observed through a lens system placed in front of eyes by creating, not an optical image projected on the retinal surface of the eye, but a rotation-based retinal image, defined as an image obtained by turning the eye-ball with respect to all object points within a field of vision and by connecting images caught at the fovea by computer simulation. The result is a simulated image perceived by the eye through the lens system.

According to this embodiment, the rotation-based retinal image is created through steps of:

creating an original image having a specific angular field of vision and entering the eye which has a specific rotational center point;

creating, by using ray tracing, a deformed original image containing deformation occurring when the original image is seen through the lens system;

determining the PSF on the retina of an eye-model caused by light from the object points of the original image in an optical system composed of the lens system and a spectacle model; and convoluting the deformed original image found in the deformed original image creating step and the PSF of each pixel of the original image found in the PSF obtaining step.

A further embodiment of the invention is characterized in that in an ocular optical system simulating method for simulating how things are seen when the outside world is observed through a lens system placed in front of an eye, comprising the steps of:

creating an original image by placing a virtual object in a virtual three-dimensional space by computer graphics, creating an image of the virtual object defined within a specific angular field of vision, entering the eye which has a specific rotational center point, and having a central line of sight of a specific direction, and obtaining an object point distance which is a distance between the position of the object point related to each pixel of the original image and the rotation center point of the eye;

creating a deformed original image containing deformation caused by the lens system by setting a passing point of the central line of sight on the lens system placed in front of the eye, by finding a ray which is emitted from the object point at the center of the field of vision, which passes through the passing point of the central line of sight, and which heads toward the rotation center point by means of ray tracing, and by finding, by means of ray tracing, the direction of a line of sight to the corresponding object point of each pixel of the original image and the lens system passing point in a field of vision after passing the lens system, wherein a field of vision in which the direction of outgoing ray of the lens system is found is defined as the field of vision after passing the lens system;

a PSF obtaining step for finding the PSF which indicates a distribution of luminance on the retina of an accommodation-dependent eye-model caused by light emitted from the object point in a combined optical system of the lens system and the eye-model turned in accordance with its principal ray direction by introducing the accommodation-dependent eye-model as the ocular optical system and by setting an accommodation state of the eye-model in accordance with the object point distance obtained in the original image creating step and the refractive power of the principal rays emitted from the object point at the lens system passing point obtained in the deformed original image creating step; and a convolution step for convoluting the image containing the deformation caused by the lens system and created in the deformed original image creating step and the PSF of each pixel obtained in the PSF obtaining step to create the rotation-based retinal image when the virtual object placed in the virtual three-dimensional space is seen by the eye at the specific position and direction of line of sight through the specific position of the lens system.

A still further embodiment of the invention is characterized in that the ocular optical system simulating method for simulating how things are seen when the outside world is observed through a lens system placed in front of eyes, comprises the steps of creating and placing a virtual object within a virtual three-dimensional space by computer graphics, creating a story seen by changing the direction of central line of sight and the lens system passing point in a time series manner, and creating a rotation-based retinal image by using the ocular optical system simulating method of one of the above embodiments at each moment in accordance with the story to create a motion picture image of the rotation-based retinal image by editing each retinal image.

Another embodiment of the invention is characterized in that in the ocular optical system simulating method according to any one of the above embodiments, the PSF obtaining step comprises steps of finding all ray data of rays emitted from the object point related to each corresponding pixel and passing each point set by uniformly dividing an entrance pupil of the eye-model by means of ray tracing and of finding the PSF as a density of distribution of spots of rays on the retina of the eye-model or as integration of diffraction based on wave optics.

A yet further invention is characterized in that, in the ocular optical system simulating method according to any one of the embodiments of the inventions, the PSF obtaining step comprises steps of setting a finite number of object sampling points in the three-dimensional space in advance, selecting a finite number of passing sampling points on the entrance pupil surface to find ray data obtained by combining all of the object sampling points and the passing sampling points by means of ray tracing to create spline interpolation coefficient data; finding ray data of rays emitted from the object point related to each corresponding pixel of the original image and passing each point set by uniformly dividing the entrance pupil by means of spline interpolation by using the spline interpolation coefficient data prepared in advance; and finding the PSF as a density of distribution of spots of rays on the retina of the eye-model or as integration of diffraction based on wave optics.

A still further embodiment of the invention is characterized in that in the ocular optical system simulating method according to any one of the second through fourth inventions, the PSF obtaining step comprises steps of approximating the PSF by a certain function to express by its parameters, selecting a finite number of object sampling points in a three-dimensional space in advance, finding PSF and its parameters of approximate function on all the object sampling points to create spline interpolation coefficient data, and of finding the PSF parameters concerning on each pixel of the original image by means of spline interpolation by using the spline interpolation coefficient data prepared in advance.

Yet another embodiment of the invention is characterized in that in the ocular optical system simulating method according to any one of the above embodiments, the rotation-based retinal image or the motion picture image of the rotation-based retinal image is displayed by image displaying means and the image displaying means indicates information regarding which position of the lens system those images have come through.

A further embodiment of the invention is characterized in that the ocular optical system simulating apparatus for simulating how things are seen when the outside world is observed through a lens system placed in front of eyes, it comprises:

an original image creating means for creating and placing a virtual object in a virtual three-dimensional space by computer graphics to create an image of the virtual object having a specific angle of field of vision and entering the eye having a specific rotation center point as an original image and to obtain an object point distance which is a distance between the position of the object point related to each pixel of the original image and the rotation center point of the eye;

a deformed original image creating means for creating a deformed original image containing deformation caused by the lens system by setting a passing point of the central line of sight on the lens system placed in front of the eyes, by finding a ray which is emitted from the object point at the center of the field of vision, which passes through the passing point of the central line of sight and which heads toward the rotation center point by means of ray tracing and by finding, by means of ray tracing, the direction of a line of sight to the corresponding object point of each pixel of the original image and the lens system passing point in a field of vision after passing the lens system, wherein a field of vision in which the direction of outgoing ray of the lens system is found is the central line of sight is defined as the field of vision after passing the lens system;

a PSF obtaining means for finding the PSF (Point Spread Function) which indicates a distribution of luminance on a retina of an accommodation-dependent eye-model caused by light emitted from the object point in a combined optical system of the lens system and the eye-model turned in accordance with its principal ray direction by introducing the accommodation-dependent eye-model as the ocular optical system and by setting an accommodation state of the eye-model in accordance with the object point distance obtained in the original image creating step and the refractive power of the principal rays emitted from the object point at the lens system passing point obtained in the deformed original image creating step; and a convolution means for convoluting the image containing the deformation caused by the lens system and created in the deformed original image creating step and the PSF of each pixel obtained in the PSF obtaining step to create the rotation-based retinal image when the virtual object placed in the virtual three-dimensional space is seen by the eye at the specific position and direction of line of sight through the specific position of the lens system.

Yet another embodiment of the invention is characterized in that in an ocular optical system simulating apparatus for simulating how things are seen when the outside world is observed through a lens system placed in front of eyes, the apparatus further comprises means for creating and placing a virtual object within a virtual three-dimensional space by computer graphics, creating a story seen by changing the direction of central line of sight and the lens system passing point in a time series manner, creating a rotation-based retinal image by using the ocular optical system simulating apparatus described in one of the above embodiments at each moment in accordance with the story to create a motion picture image of the rotation-based retinal image by editing each retinal image.

A still further embodiment of the invention is characterized in that in the ocular optical system simulating apparatus described above further comprises image displaying means for displaying the rotation-based retinal image or the motion image of the rotation-based retinal image and indicating information that which position of the lens system those images have come through.

While the invention has been described in detail, further objects, features, and advantages of the invention will become apparent from the Detailed Description of the Preferred Embodiments when considered together with the attached Drawings and Examples.

BRIEF DESCRIPTION OF THE DRAWINGS

The claim of this patent contains at least one drawing executed in color. Copies of this color drawing(s) will be provided by the Patent and Trademark Office upon request and payment of the necessary fee.

FIG. 3 shows a coordinate system of the rotation-based retinal image (RRI) while wearing a lens system.

FIG. 4 is a table showing the optical parameters (non-accommodated state) of Navarrols eye simulation.

FIG. 5 is a table showing expressions of dependence on control power of a crystalline lens of the Navarro's eye simulation.

DETAILED DESCRIPTION OF THE PREFERRED EMBODIMENTS

First Embodiment

The ocular optical system simulating method of a preferred embodiment is a method for obtaining a still image of a rotation-based retinal image when an image of a three-dimensional object created by computer graphics is seen through a lens. A rotation-based retinal image (RRI) is an image obtained by approximately reproducing an image perceived by eyes by image-processing the image of the three-dimensional object by considering optical effects based on certain assumptions found by the inventors. That is, the rotation-based retinal image is not an optical image projected on the retinal surface of the eye but is what is defined as an image obtained by rotating eye-balls with respect to all object points within the field of vision and by connecting images caught at the fovea.

The ocular optical system simulating method of the first embodiment comprises roughly (1) creating an original image, (2) creating a deformed original image, (3) determining a PSF, and (4) convoluting the deformed original image with the PSF.

(1) Original Image Creating Step

This step comprises placing a virtual object within a virtual three-dimensional space by computer graphics and creating an image of a specific angular field of vision of the virtual object entering an eye whose rotational center point is placed at a specific position and which has a specific direction of a central line of sight. The resultant image is called the original image. This step also involves measuring an object point distance which is a distance between the position of the object point related to each pixel of the original image and the rotational center point of the eye.

a) Creating Virtual Object Image which is the Basis of the Original Image

At first, the virtual three-dimensional object is created and placed in the virtual three-dimensional space by a known method of computer graphics. For example, an image is created in which a desk, a chair, furniture, etc., are placed within a room and a flower bed, trees and signs are placed on the outside.

b) Creating Original Image

Figure 1:
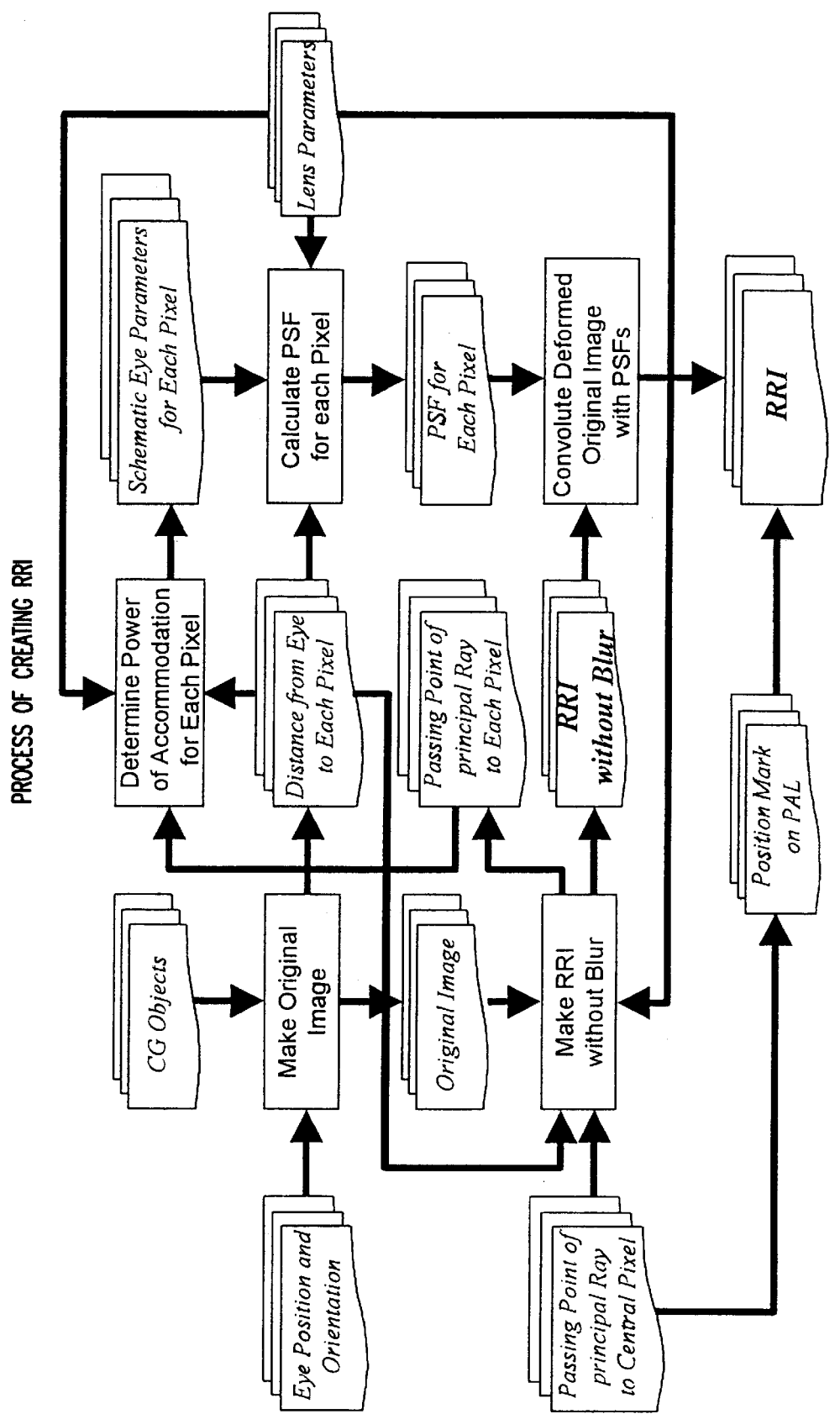
FIG. 1 is a flowchart showing creation of a rotation-based retinal image (RRI).
Figure 2:
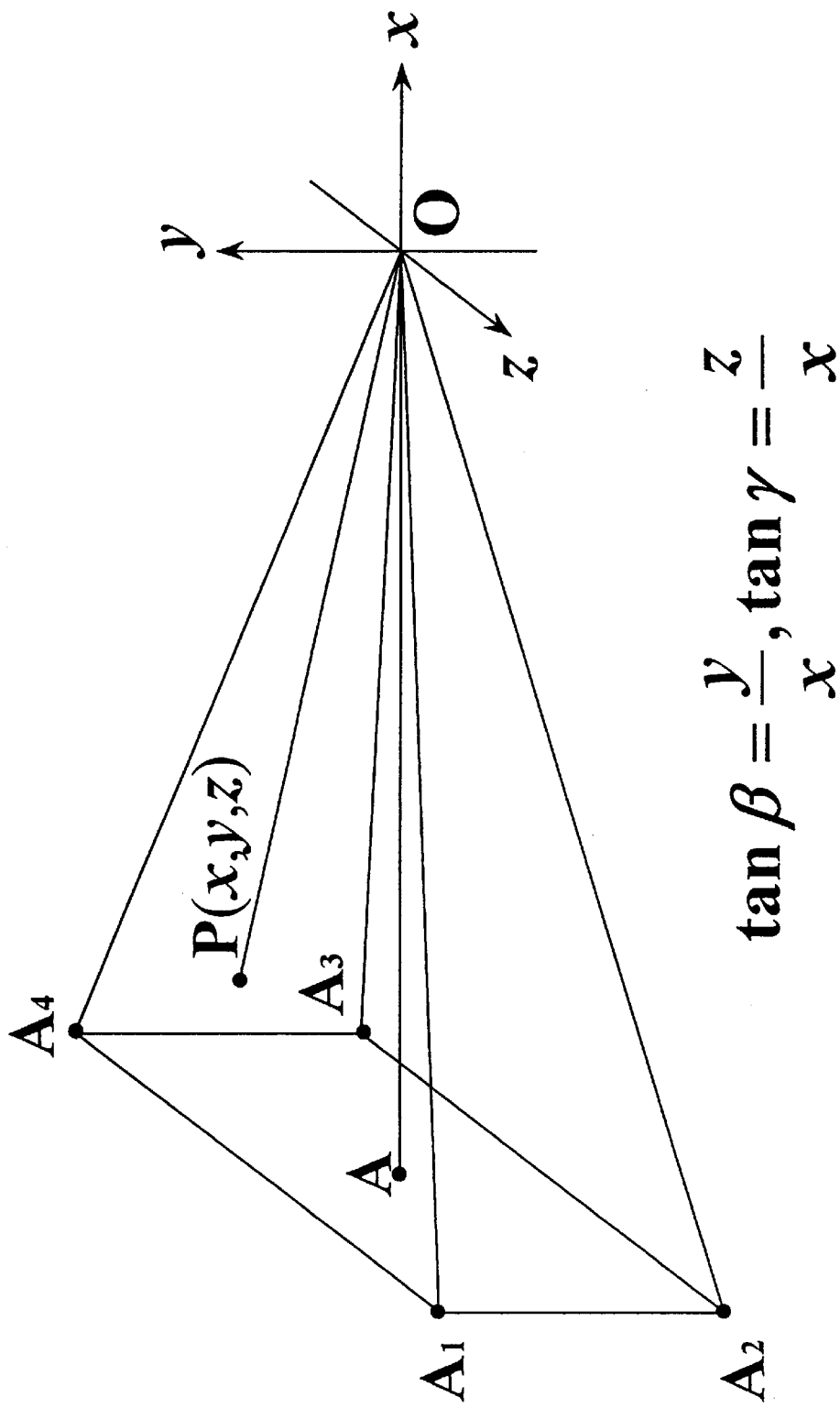
FIG. 2 shows a coordinate system of the rotation-based retinal image (RRI).

The image of the specific angle of vision of the virtual object entering the eye whose rotational center point is placed at a specific position and which has a central line of sight in a specific direction is the original image. That is, as shown in FIG. 2, a pyramidal field of vision A1, A2, A3 and A4 is set as the specific field of vision. The center A of the pyramidal field of vision A1, A2, A3 and A4 is the center of the field of vision. The line connecting A with the center of rotation O is the central line of sight. This line is defined as an x-axis with O as its origin. Then, coordinates of the rotation of the retina at an arbitrary point P(x,y,z) which is an arbitrary object point within the pyramidal field of vision is set as $\mu=\tan\beta=y/x$, $v=\tan\Gamma=z/x$. Here, $\beta$ and $\gamma$ are azimuths of P(x,y,z). When each object point within the field of vision is represented by this coordinate system, an arbitrary straight line in the space is reflected as a straight line on the rotation-based retinal image. The image representing each object point within this coordinate system is the original image. Each object point distance is found from the coordinate values of P(x,y,z).

(2) Deformed Original Image Creating Step

This step comprises determining a passing point of the central line of sight on a lens system placed in front of the eye. The passing point is determined by finding, by a ray tracing method, the point at which a ray emitted from the object point at the center of the field of vision, passes through the lens and then is coincident with the central line of sight before heading toward the rotational center point of the eye. In this way, one can also find the direction of a line of sight to the object point, and the lens system passing point corresponding to each pixel of the original image in a field of vision after passing the lens system. In this case, the direction of an outgoing ray of the lens system (i.e., after passing the lens system) corresponding to a ray originating at the center of the field of vision before the lens system is defined as the central line of sight. In this way, a ray tracing method is used to create an image containing deformation caused by the lens system.

That is, as shown in FIG. 3, a lens L is placed at the position close to the origin O between the origin O and A in FIG. 2. The ray emitted from the object point within the pyramidal field of vision is refracted by the lens L and reaches the origin O. Accordingly, the eye-ball must be turned to the direction of OB in order to gaze steadily at the point A. The pyramidal field of vision representing the field of vision is also changed to B1, B2, B3 and B4 (the field of vision after passing the lens system). The rotation-based retinal image must have a coordinate system in which an x' axis is the line of sight. This coordinate system is found by means of ray tracing by taking the refractive power of each point of the lens into consideration and the image caused by the object point coordinate thus found is defined as the deformed original image.

It is noted that the relative positional relationship of the coordinates on the rotation-based retinal image of each point within the field of vision changes through the lens, differing from the case of naked eyes. This is a cause of the deformation of the spectacle lens. The direction of OB changes depending on the position on the lens used. The change can be especially abrupt in the case of a progressive addition lens. The angle of other rays within the field of vision entering the eye also changes and that change is particularly uneven in the case of a graduated lens. This uneven change is perceived as fluctuation and deformation.

(3) PSF Obtaining Step

This step is, simply said, a step of determining how an image is blurred when a specific object point is observed through a specific position on the lens system. The PSF (Point Spread Function) is a distribution of brightness on the retina originated from the object point. It represents the degree of blur and may be calculated tracing a large number of rays in the combined optical system of the lens system and the eye-model rotated corresponding to the direction of the output principal ray. Before calculating the PSF, the accommodation should be introduced into the eye-model in accordance with the object point distance obtained in the original image creating step, and the refractive power of the lens system at the passing point obtained in the deformed original image creating step. The following explains how to calculate the PSF.

(a) Introducing an Accommodation into the Corresponding Eye-model

Because the image formed on the retina from the deformed original image via the ocular optical system is the rotation-based retinal image, it is necessary to introduce an ocular optical system model. In this case, because the eyes have an accommodating action corresponding to an object distance, the accommodating action must be also taken into consideration. The present embodiment uses an accommodation dependent eye-model of R. Navarro et al. which is an eye-model in which the accommodating action has been taken into consideration. In the Navarro model, not only paraxial values but also spherical aberration and chromatic aberration are adjusted to actually measured values of the eye. The model is simply composed of four planes and three planes among them are aspheric surfaces of a quadratic curve. A crystalline lens does not have a refraction distributed structure and its tracing calculations are easy to accomplish. The radius of curvature, thickness and aspheric degree change are proportional to the logarithm of the accommodation power. FIG. 4 shows optical parameters of the Navarro's accommodation dependent eye-model when no accommodation is made. FIG. 5 shows equations of the dependence of the parameters on the accommodation. The aspherical surface may be expressed by $$y^2+z^2+(1+Q)x^2-2Rx=0,$$

where Q is asphericity.

(b) Calculating the PSF (i) Meaning of PSF

Figure 6A:
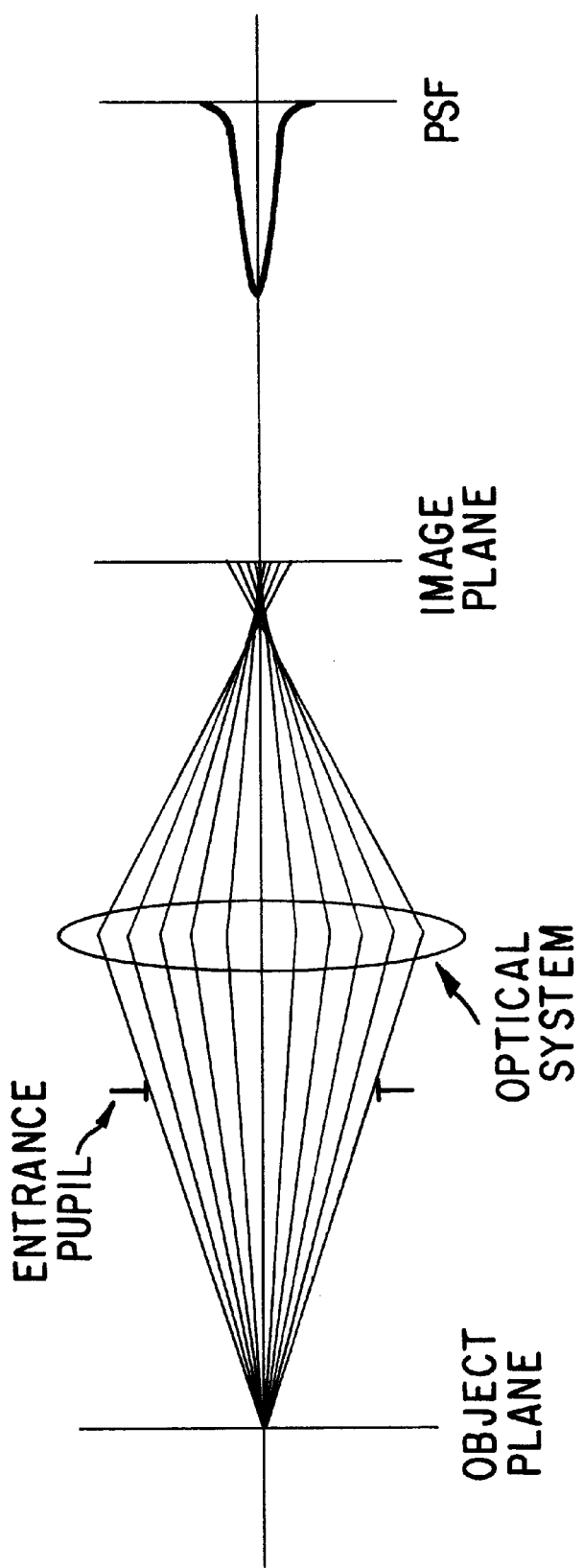
FIG. 6 is a diagram for explaining the PSF.
Figure 6B:
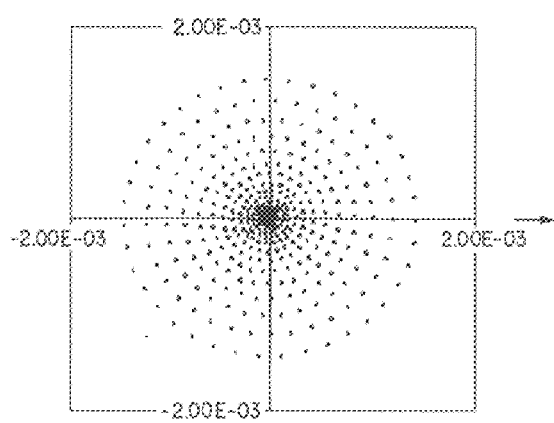
Figure 6C:
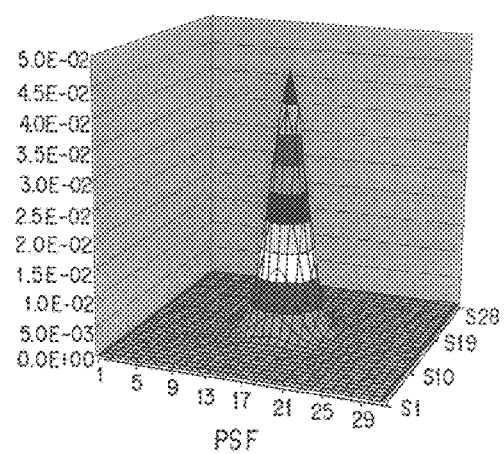

Generally, an optical image created by an optical system may be found by finding the PSF (Point Spread Function) of the optical system and by convoluting the PSF with an actual image. As shown in FIG. 6, the PSF is a function representing a state of aggregation of a spot of an image forming plane where rays emitted from one point of an actual object are condensed and may be expressed as a number of spots per unit area. Although all of the spots of the PSF would gather at a single image forming point if the optical system were perfect and its distribution would turn out to be a vertical straight line, the PSF normally assumes a shape similar to a spread-out Gaussian distribution. Because the object may be considered to be composed of spots, its image may be obtained by the distribution of luminance of the object and the convolution of the PSF.

(ii) PSF Calculating Method

Figure 7:
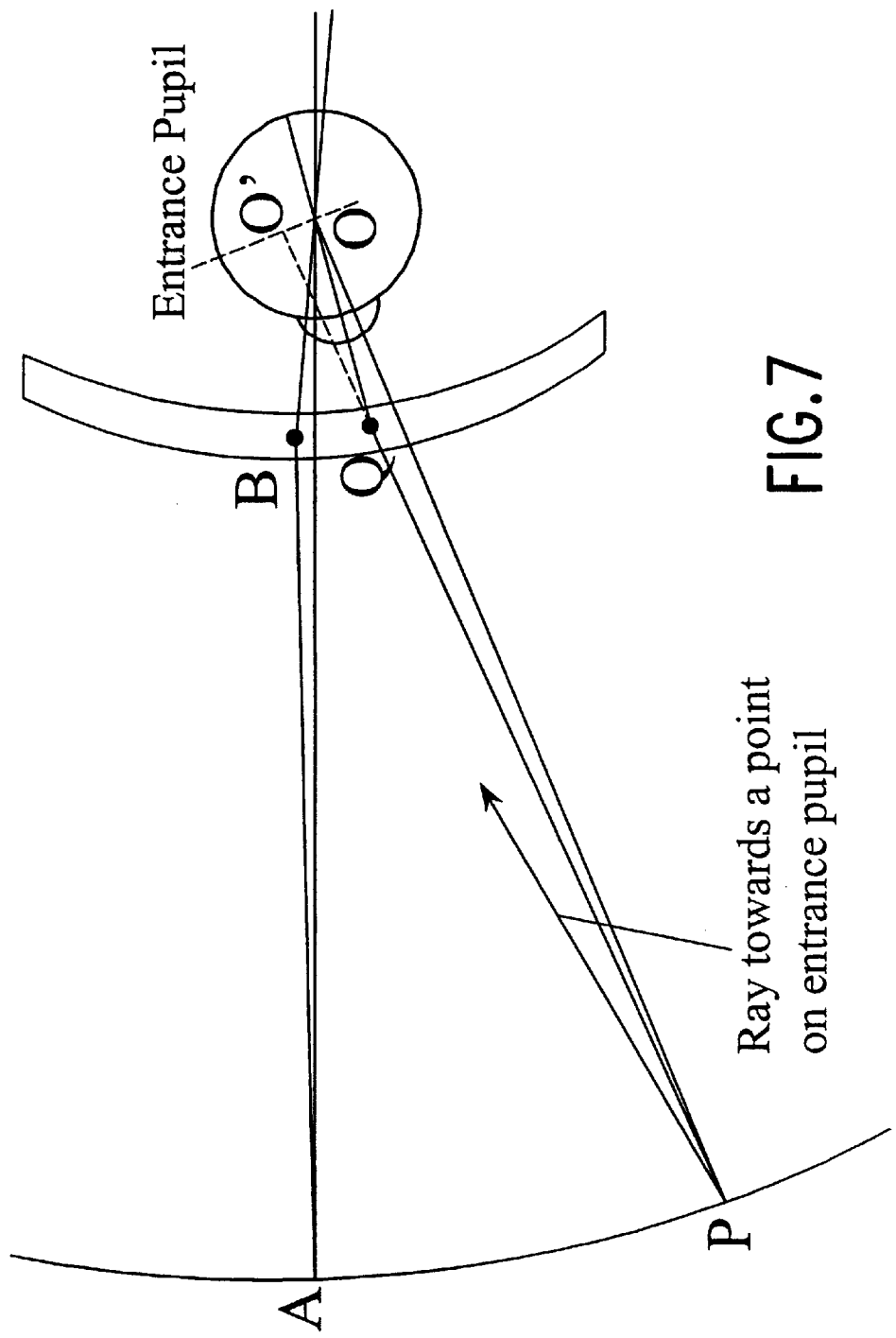
FIG. 7 is a diagram showing the relationship between ray tracing and an entrance pupil.

FIG. 7 shows the relationship between ray tracing and the entrance pupil in an optical system for finding the PSF when an object point P is seen through a point Q on a lens. The ray from the object point P is refracted at the point Q on the surface of the lens and reaches the rotation point O after changing its outgoing direction. It seems, for the eye, that the object point P is on an extension line of the direction of the outgoing ray QO. Thus, the viewer sees the point P by turning an optical axis of the eye-ball in the QO direction at first and by accommodating by deciding a degree of accommodation corresponding to a distance to the point P and to the refracting power at the point Q. The optical system is fixed at this moment and the PSF may be found.

As described above, the PSF is a density of spots on the image forming plane of the rays emitted from the object point and passing the center of a large number of equally divided regions of the entrance pupil. Strictly speaking, the entrance pupil is located at a conjugate point of the pupil on the object side. However, the position of the pupil changes due to the rotation and the position of the conjugate point, and differs depending on the accommodation state. Meanwhile, the position of the center of rotation is fixed and a distance from the center of rotation to the conjugate point of the pupil is very small compared to the distance to the object. Accordingly, there is no problem with considering the position of the entrance pupil to be the center of rotation in case of naked eyes. Although the entrance pupil of the whole optical system is the conjugate point of the center of rotation with respect to the spectacle lens, the power is different depending on the passing point in case of the progressive addition lens and its position changes subtly. Because its variation is also very small as compared to the distance to the object, the entrance pupil may be assumed to be located at point O' on the extension line PQ and to be PO=PO'.

Figure 8A:
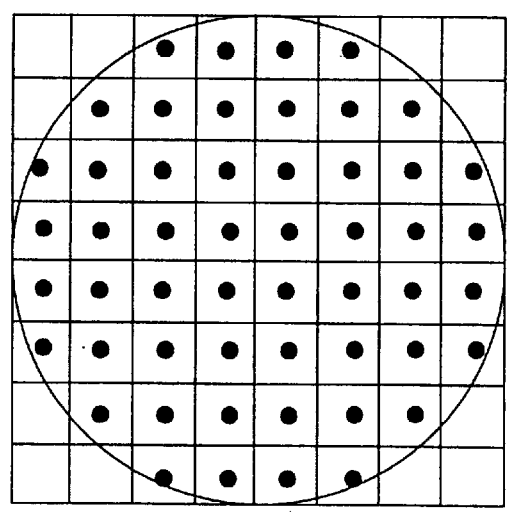
FIG. 8 is a diagram showing methods for dividing the entrance pupil.
Figure 8B:
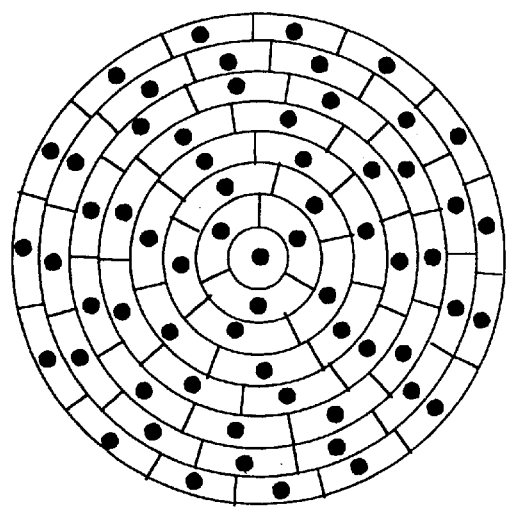

It is essential to divide the entrance pupil into a large number of uniformly distributed small regions to find the PSF accurately. There are two kinds of dividing methods: (1) a latticed dividing method and (2) a ringed zone dividing method, as shown in FIGS. 8A and 8B. Although the latticed dividing method allows good uniformity to be obtained, it permits tracking of only about 70% of scheduled rays because it has useless parts at its four corners. Meanwhile, the ringed zone dividing method allows rays to be tracked by the ringed zones and allows the uniformity of spots to be improved by controlling a phase angle of the ringed zone. The ringed zone dividing method has therefore been adopted in the present embodiment.

Figure 9:
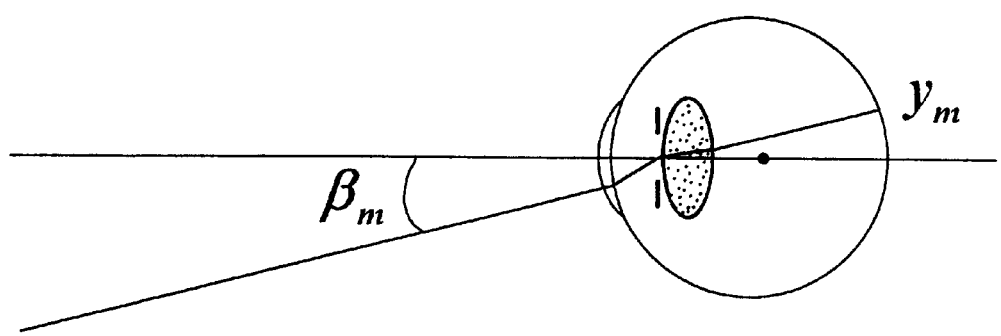
FIG. 9 is a diagram showing the position of the retina and an angle of incidence.

The PSF may be obtained by tracing the large number of rays emitted from the object point and passing the equally divided points of the entrance pupil and by counting the spots on the retinal surface. However, this PSF is a function of the position of the retina $(y_m, z_m)$ and convolution cannot be implemented directly with the rotation-based retinal image whose coordinate is the tangent $(\mu, v)$ of the angle of rotation. Accordingly, it is necessary to find an angle of an incident ray corresponding to the position of the retina. Because $(y_m, z_m)$ is close to the optical axis in most cases, the expression of paraxial rays may be applied. That is, as shown in FIG. 9, angles of deviation $(\beta_m, \gamma_m)$ from the optical axis of the incident ray corresponding to $(y_m, z_m)$ are $\tan\beta_m = y_m/f$ and $\tan\gamma_m = z_m/f$, where $f$ is a focal distance of the eye-ball. Strictly speaking, although the relational expression of the incident angle and the position of the retina changes depending on the distance to the object and the eye accommodation state, the distance to the object is very long as compared to the focal distance in case of eyes, and may be considered to be a point at infinity.

Considering the case of FIG. 7 when the arbitrary object point P is seen, an angle from the line of sight corresponding to the position of the retina $(y_m, z_m)$ is deviated by $(\beta, \gamma)$ further from the angle of direction of P $(\beta_m, \gamma_m)$. What must be noticed here is that the angle is not $(\beta+\beta_m, \gamma+\gamma_m)$ in general and must be found by using Listing's law of rotation. This enables transformation of the PSF $p(\mu, v)$ on the retina found by ray tracing into PSF $p(y_m, z_m)$ on the coordinate of incident ray angle and enables convolution with the distribution of luminance of the object.

Figure 10:
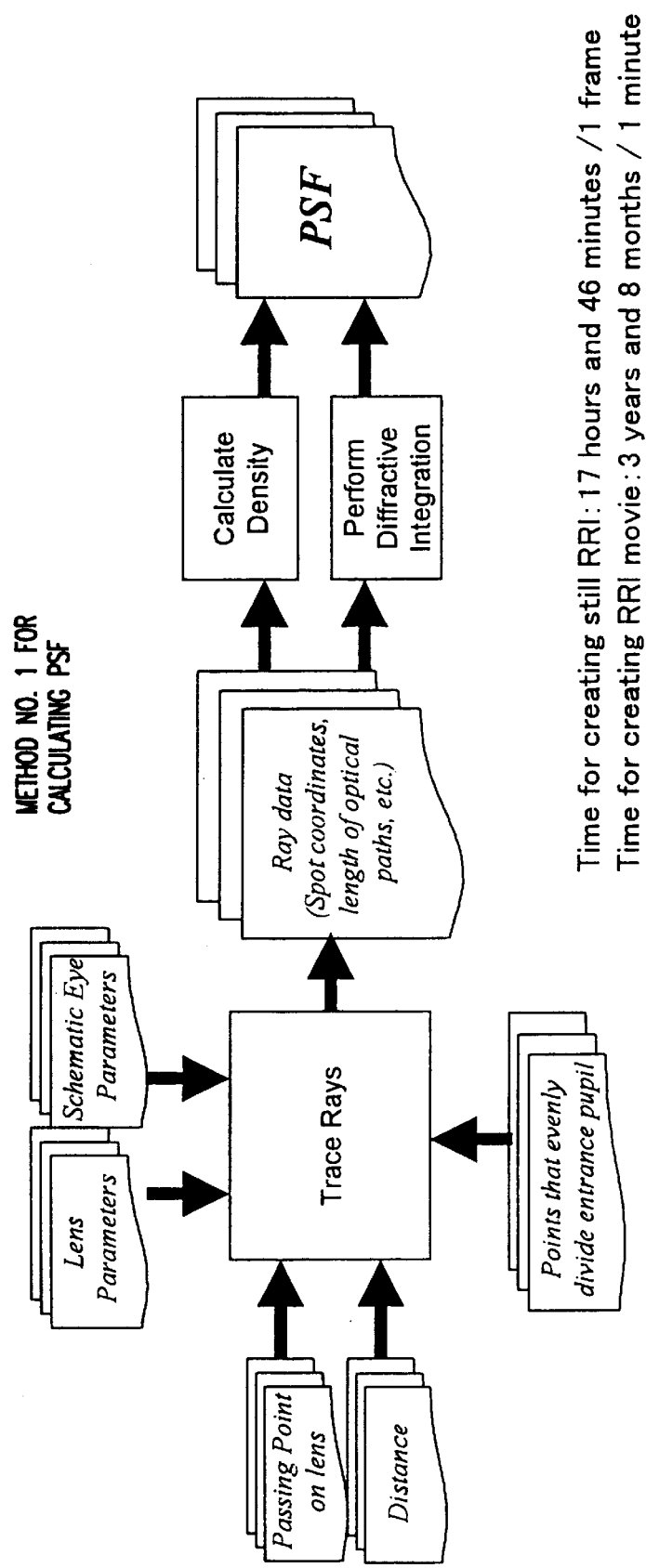
FIG. 10 is a chart showing a first method for obtaining the PSF.

FIG. 10 summarizes the procedure for obtaining the PSF described above schematically as a first method for obtaining the PSF. In short, for each object point, the distance from the entrance pupil, and passing point on the lens, lens parameters and schematic eye parameters are used in the process of ray tracing. According to the above described embodiment, the entrance pupil is evenly divided, and ray data are then obtained. The ray data corresponds to spot coordinates, length of optical paths, etc. Using this ray data, the PSF is then calculated using either density calculations, or diffractive integration.

(4) Convolution Step

The deformed original image, containing deformation caused by the lens system and created in the deformed original image creating step, is convoluted with the PSF of each pixel obtained in the PSF obtaining step, to create a rotation-based retinal image, when the virtual object placed in the virtual three-dimensional space is seen by the eye at a specific position and in the direction of specific line of sight through a specific position of the lens system. The convolution is carried out, for example, as follows. When a distribution of intensity of light of the deformed original image is f(u,v) and for each point (u,v) there exist a PSF whose value at its neighboring point $(\mu_0, v_0)$ is expressed as $p(u, v, \mu_0-u, v_0-v)$, the intensity of light at the point $(\mu_0, v_p)$ on the retina may be expressed by the following expression:

Equation 1

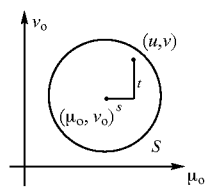

$$g(\mu_o, v_o) = \int\int_S f(u, v) p(u, v, \mu_o - u, v_o - v) du dv$$

Where point (u,v) locates within a domain S within which its PSF has non-zero value at point $(\mu_0, v_0)$. The equation means that the light intensity of the RRI the accumulation of light spread from each point (u,v) within the domain S. A still image of the rotation-based retinal image may be obtained by finding the intensity of light at all points on the retina by using this equation.

EXAMPLES

Several static RRI's were created according to the present invention, but the process could equally well demonstrate the actual animation of an RRI by the creation of a story line in which the central line of sight of a field of vision and the point through which the central line of sight passes through the lens changes with time.

A progressive additional lens (PAL) used in the example simulation was HOYALUX GP-wide S0.00C0.00ADD2.00 for right eye (Hoya Co., Ltd.). The maximum power of accommodation was set to be 1.00 diopters.

Figure 11:
FIG. 11 shows an example of a rotation-based retinal image (RRI) obtained from an original image of an outdoor scene according to the present invention.

FIG. 11 is a rotation based retinal image (RRI) created according to the present invention in which the original image is an outside scene. The PAL mark in the upper-right corner shows the area that the field of vision passes through the lens. The red point indicates the position of central line of sight. The red rectangle expresses the extent of the field of vision, which is approximately 100 degrees wide and 83.6 degrees high. The exact shape of the corresponding lens area is deformed from a rectangle because of the complicated refraction of the lens, as shown, for example in FIG. 3. In this scene the horizontal lines in the near area are bent by the near part of the PAL. Poles on two sides are bent and declined. These phenomena often occur in early days of wearing a PAL. The position and degree of blurs are in accordance with the distribution of transmitted astigmatism.

Figure 12:
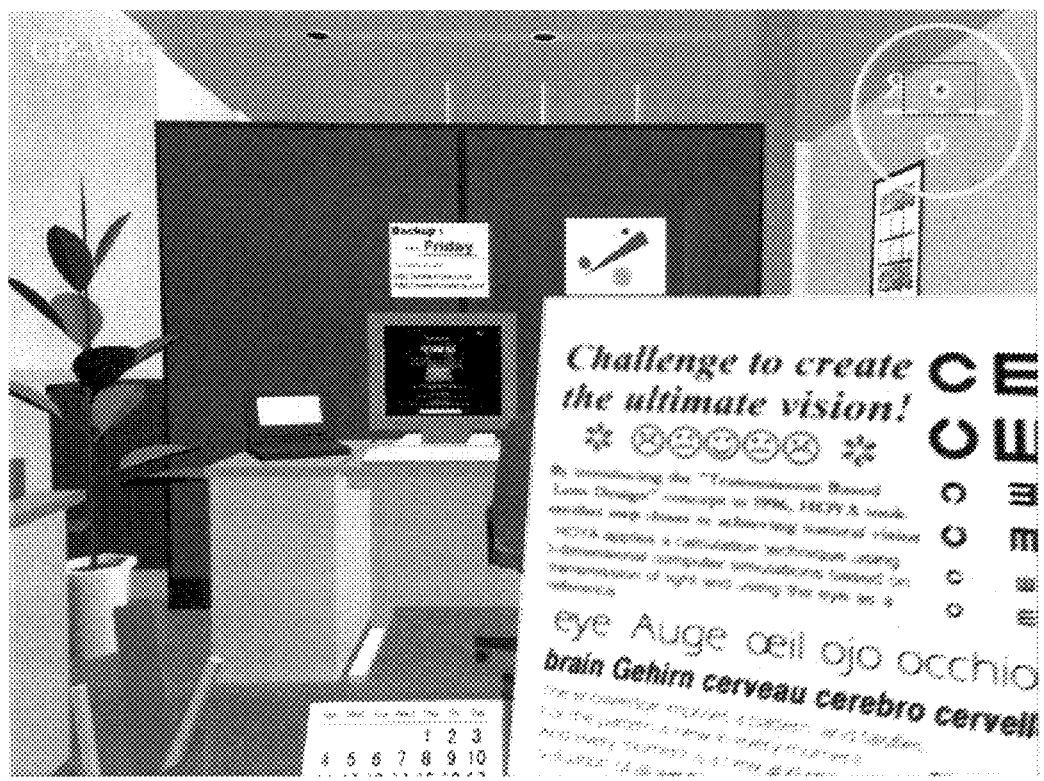
FIG. 12 shows another example of a rotation-based retinal image (RRI) obtained from an original image of a room according to the present invention.

FIG. 12 is a rotation based retinal image created according to the present invention in which the original image is a room, and the scene is viewed through the distance vision area of the PAL. The field of vision is approximately 50 degrees wide and 38.6 degrees high. In this rotation based retinal image, for example, the poster on the wall and other distant objects are clear while the chart in front of the eye is blurred.

Figure 13:
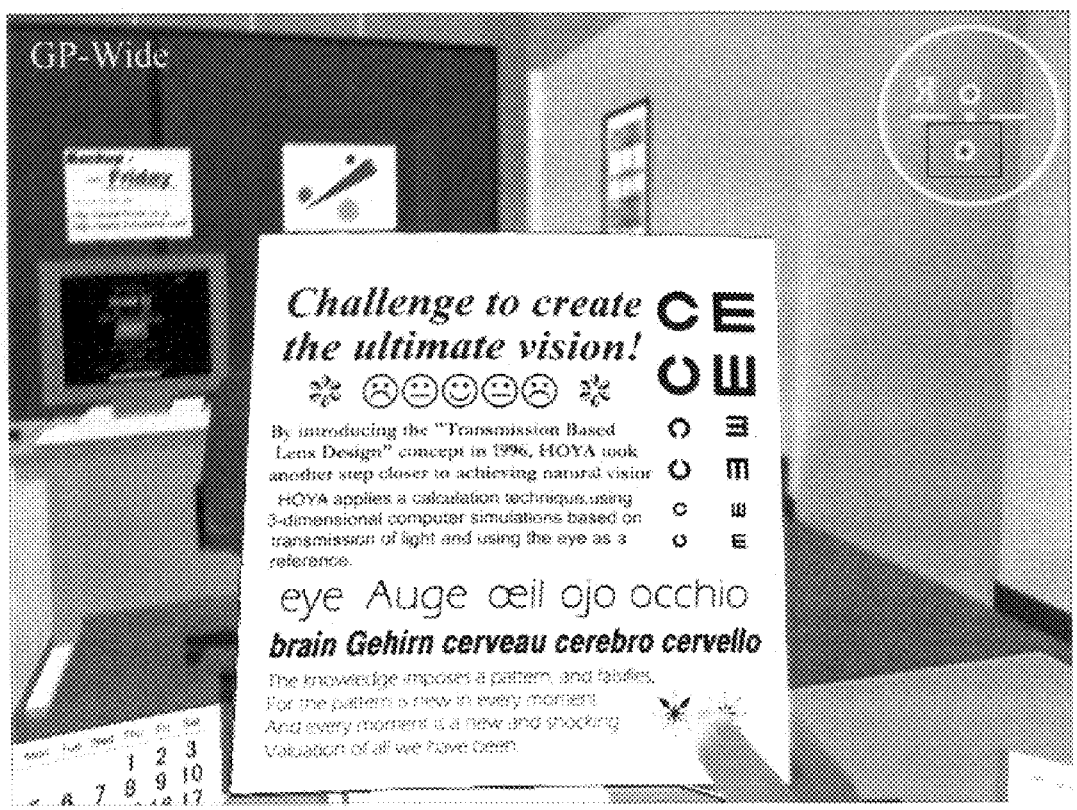
FIG. 13 shows another example of a rotation-based retinal image (RRI) obtained from an original image of a room according to the present invention.

FIG. 13 is a rotation based retinal image created according to the present invention in which the original image is a scene in a room, and the image is viewed through the near vision area of the PAL. The field of vision is the same size as in FIG. 12. The chart in front of the eye is clear while all distant objects are blurred.

Figure 14:
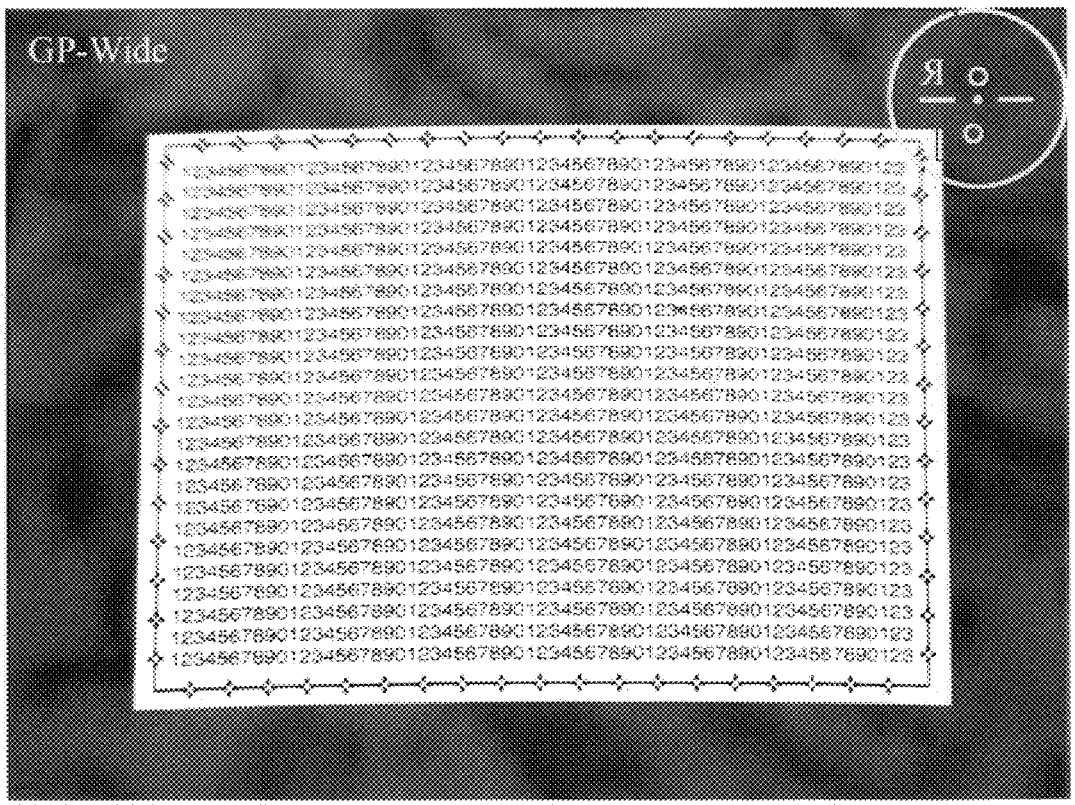
FIG. 14 shows another example of a rotation-based retinal image (RRI) obtained from an original image of a character chart according to the present invention.

FIG. 14 shows the RRI of an original image seen at close range through the reading area of the PAL. The field of vision is the same size as FIGS. 12 and 13, that is, 50° horizontal and 38.50 vertical. The original image is a character chart placed 333 mm from the eye, such as might be the case for example, if the placed on a desk in front of the viewer. The chart is A4 size (297 mm×210 mm). As stated above, the PAL is a HOYALUX GP (Trademark of Hoya Co., Ltd.) for the right eye and far-use 0.00 D and added 2.00 D. The circle at the upper right corner indicates the position of the point of the lens where the central line of sight passes through. Although the position of the passing point is not discernible in the figure, it is indicated by a red point within the circle. The circle represents a profile of the lens and the point at the center of the circle indicates a geometrical center of the lens and round marks above and below the geometrical center indicate a far-use measuring point (above) and a near-use measuring point (below). The reversed character R indicates that the lens is a right lens. The example in FIG. 14 is a case when the lens passing point of the central line of sight is located above the near-use measuring point (lower circle). The distinctness of characters is in accordance with the distribution of transmitted astigmatism. It can be seen that blur and deformation at the right and left are faithfully reproduced.

The present embodiment enables obtaining an image in which blur and deformation perceived when things are seen through the lens system such as a progressive addition lens or PAL are approximately reproduced. That is, although the whole field of vision can be perceived clearly by healthy naked eyes, only part of the field of vision is seen clearly and other parts are seen with blur and deformation when a presbyope wears the PAL. The present embodiment allows the perception of a presbyope to be reproduced as an image. Accordingly, it enables the designer who does not have presbyopic eyes to confirm how things can be seen by a particular progressive addition lens or PAL, thus enabling the most desirable evaluation, by displaying the image thus obtained on a display unit, as for example, illustrated in FIGS. 11–14.

Second Embodiment

Figure 15:
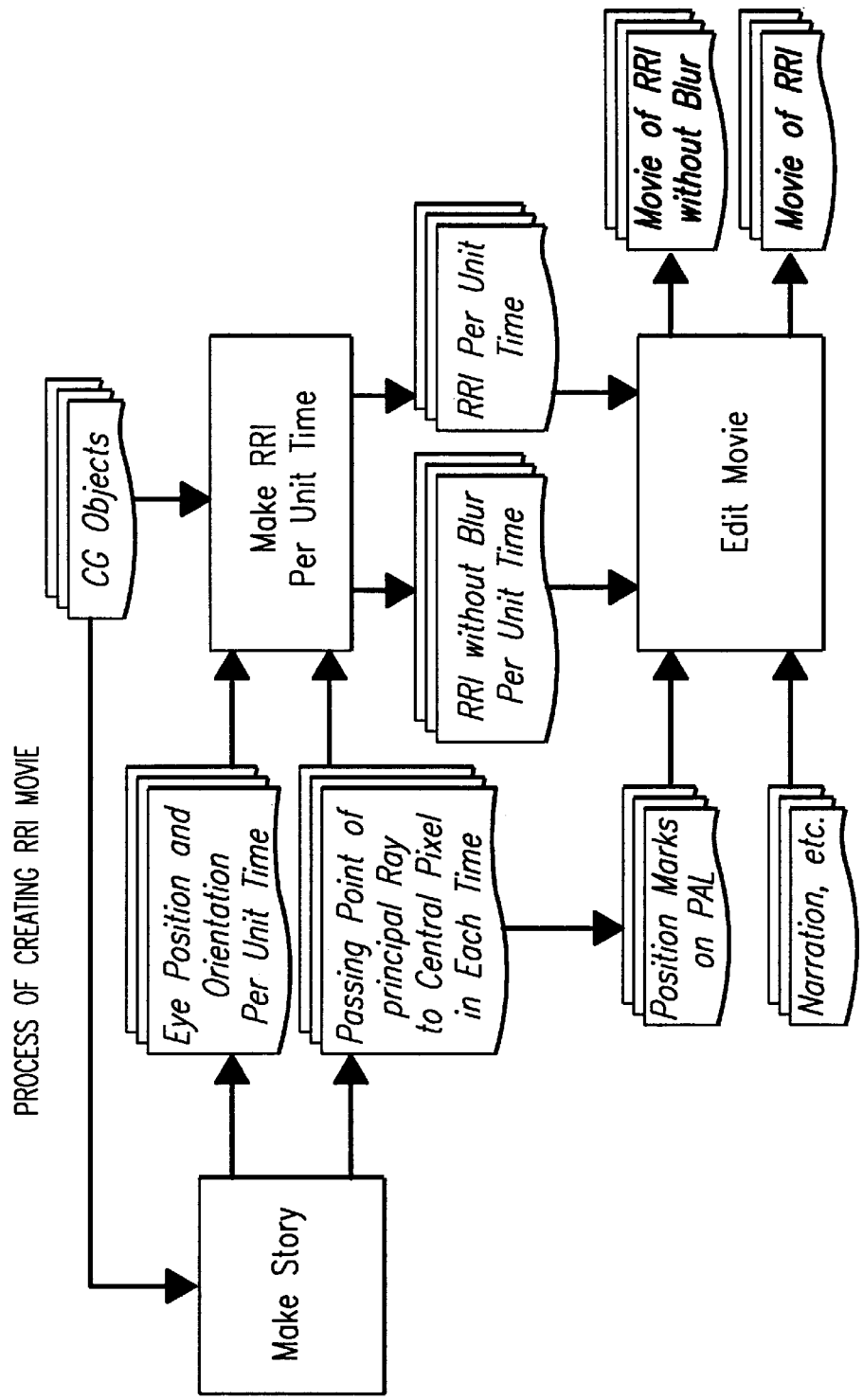
FIG. 15 is a flowchart showing creation of a motion image of the rotation-based retinal image.
Figure 16:
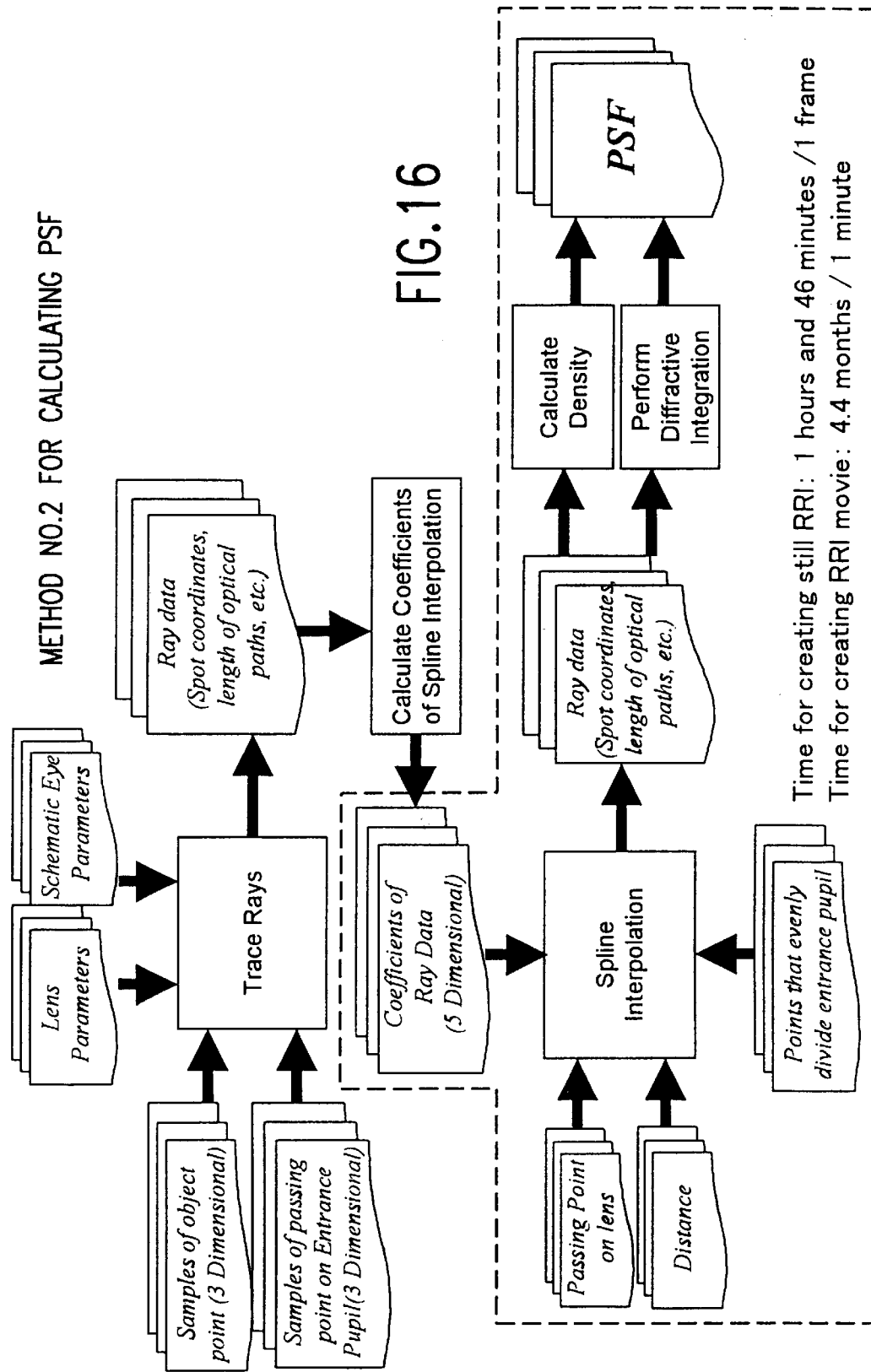
FIG. 16 is a chart showing a second method for obtaining the PSF.

This embodiment is a case of creating a large number of still images of the rotation-based retinal image in a time-series manner while changing the position and direction of the central line of sight of an eye to obtain a motion picture of the rotation-based retinal image. Accordingly, the present embodiment is basically the same as the first embodiment except that, when creating the original image, a step of creating a story of how the position and the direction of the line of sight of the eye are changed and a step of editing individual still images obtained in the time-series manner to make the motion picture are added, so that a chart showing the overall flow thereof is clearly shown in FIG. 15 and a detailed explanation is unnecessary. It is noted that a story of a lens passing point is also necessary of course for the story. Further, as for a method for creating the story, it is possible to realize smooth movement of the line of sight not by defining the position and the direction of line of sight of the eye and the lens passing point at all times but by adopting spline interpolation.

The step, which takes the most time for computing process, etc., is the PSF obtaining step in the present embodiment. In particular, because the PSF in the whole direction of line of sight is different when the lens system is a progressive addition lens, it is necessary to find the PSF for all pixels. For instance, it is necessary to perform a calculation of ray tracing 192,000,000 times on the whole when a number of rays to be tracked in finding the PSF is set to be 400 (not so many) in an image of 800×600 pixels. When the computing ability of a computer is assumed to be 3,000 rays per second, it takes 64,000 seconds, i.e., 17 hours 46 minutes and 40 seconds, though it depends on complexity of planes of the lens system and the number of planes. This is the computing time when the time required for convolution and other functions is not taken into account. Because the target of the simulation of this time is a motion image, 1,800 images have to be simulated in order to create one minute of picture having 30 frames per second. Thus, it would take 32,000 hours=1,333 days, i.e., about 3 years and 8 months, for ray tracing only. Accordingly, although it is theoretically possible to find the PSF by relying only on ray tracing, this is not practical when the enormous amount of computational time required is considered.

As a result, the inventors have decided not to implement ray tracing for all of the object points but to implement ray tracing only for sampled points and to find other points by spline interpolation. Although an arbitrary point A in a space may be expressed by orthogonal coordinates (x,y,z), it is more appropriate to express it by an inverse number D of a distance from the rotation point and tangents $\mu_i$, $v_i$ of the azimuth, because the distance from the eye is important in the case of spectacles. The result is as follows:

Equation 2

$$D = \frac{1}{\sqrt{x^2 + y^2 + z^2}}, \mu_i = \frac{y}{x}, v_i = \frac{z}{x}$$

Ray data (the direction in output space ($\mu_0$,$v_0$) optical path, etc.) obtained by tracing an arbitrary ray emitted from the point A, i.e., a ray passing through an arbitrary point ($y_p$,$z_p$) on a plane of a tentative entrance pupil, are functions of D,$\mu_i$,$v_i$,$y_p$,$z_p$. That is, they may be expressed as $\mu_0 = \mu_0$(D, $\mu_i$,$v_i$,$y_p$,$z_p$), $v_0 = v_0$(D,$\mu_i$,$v_i$,$y_p$,$z_p$), etc. A dimension of wavelength may be further added when chromatic aberration is taken into account. The ray data of arbitrary points within a predetermined range (five-dimensional box) may be found by spline interpolation by setting an appropriate number of sampling points at adequate positions within the predetermined range of each of the variables D,$\mu_i$,$v_i$,$y_p$,$z_p$ and by implementing ray tracing with respect to all the sampling points on the five-dimensional lattices in advance to find the ray data.

Next, the increase of computing speed of the spline interpolation will be discussed. One-dimensional spline interpolation may be expressed as follows.

Equation 3

$$F(x) = \sum_{i=1}^{n} C_i N_i(x)$$

where, i is a node number in each dimension, $C_i$ is its coefficient, and n is a number of sampling points. $N_i(x)$ is a base function corresponding to an i-th node, has a value other than zero in a range between the i-th node and i+M -th node when the rank is M, and is expressed by a M−1-th degree polynominal between the adjacent nodes (locality of base function) In other words, only M $N_i(x)$ other than zero at most exist in an arbitrary point a within a domain of x. Accordingly, although there seem to be n terms of interpolation equations at a glance, it is actually M terms when x=a and F(a) may be obtained by M multiplication operations and M addition operations. The five-dimensional spline interpolation may be expressed as follows:

Equation 4

$$F(D, \mu_i, v_i, y_p, z_p) = \sum_{i,j,k,l,m} C_{i,j,k,l,m} N_m(z_p) N_l(y_p) N_k(v_i) N_j(\mu_i) N_i(D)$$

Where, i, j, k, l and m are node numbers of each dimension and only the number of sampling points changes. That is, the number of terms is a product of the number of sampling points of each dimension. However, due to the locality of the base function described above, the number of terms other than zero is a product of ranks of each dimension for one point. When a spline rank in each dimension is 4, the number of terms is $4^5$=1024. That is, in one interpolation computation, 1024 addition operations and 1024 multiplication operations are carried out. In general, the number of multiplication operations required for computation of spline interpolation of M ranks in J dimensions is J×$M_J$ and the burden of computation increases sharply as the number of dimensions increases. However, the computations may be reduced by rewriting the above equation as follows:

Equation 5

$$F(D, \mu_i, v_i, y_p, z_p) =$$
$$\sum_i \left( \sum_j \left( \sum_k \left( \sum_l \left( \sum_m C_{i,j,k,l,m} N_m(z_p) \right) N_l(y_p) \right) N_k(v_i) \right) N_j(\mu_i) \right) N_i(D)$$

Equation 5 is a nest structure of one-dimensional interpolation and the order of the dimensions may be changed freely. The number of multiplication and addition operations is 4+4×(4+4×(4+4×(4+4×4)))=1364 operations and they may be done in almost ⅓ of the computing time. In general, the number of multiplication operations necessary for a M-rank spline interpolation computation of the J dimension turns out as follows:

Equation 6

$$\sum_{i=1}^{J} M^i = \frac{M}{M-1}(M^J - 1)$$

The amount of computation is still large and is not practical even when such a method is adopted. In general, it may be difficult to reduce the computing time of the multi-dimensional spline interpolation further than the above-mentioned method. However, there is a method for reducing it further in finding the PSF due to its special properties. Ray data connecting with a large number (e.g., 400) of points on the surface of entrance pupil ($y_p$-$z_p$ plane) is required to find the PSF at one point ($D_0$,$\mu_{i0}$,$v_{i0}$) on an object. A like value is substituted to a three-dimensional variable of 400 times of the five-dimensional spline interpolation. When the interpolation of 400 times is carried out by two-dimensional spline interpolation, the computing time may be reduced considerably. The five-dimensional spline interpolation equation is rewritten as follows:

Equation 7

$$F_0(y_p, z_p) = F(D_0, \mu_{i0}, v_{i0}, y_p, z_p) = \sum_{l,m} E_{l,m} N_m(z_p) N_l(y_p)$$

$$E_{l,m} = \sum_{i,j,k} C_{i,j,k,l,m} N_k(v_{i0}) N_j(\mu_{i0}) N_i(D_0)$$

Equation 7 shows a method of finding a two-dimensional space when variables of three-dimensions are defined in the five-dimensional spline space. Here, the two-dimensional spline is called a degenerate space of the point ($D_0$,$\mu_{i0}$,$v_{i0}$) and $E_{l,m}$s are coefficients of the degenerate spline. The nodes and the base function of the degenerate spline are all the same as those of the five-dimensional spline. The number of $E_{l,m}$ is a product of the numbers of sampling points and it is 81 when 9 sampling points are set for the both dimensions of $y_p$ and $z_p$. The three-dimensional spline interpolation is used as shown in the equation to find each coefficient. Then, ray data of an arbitrary point on the $y_p$-$z_p$ plane may be calculated by two-dimensional interpolation by using $c_{l,m}$ thus obtained. Accordingly, the PSF at the point c may be obtained just by computing the three-dimensional interpolation 81 times and the two-dimensional interpolation 400 times. The number of multiplication operations is $$81 \times \frac{4}{4-1}(4^3 - 1) + 400 \times \frac{4}{4-1}(4^2 - 1) = 14084$$

and is about 37 operations per one ray. The effect on reducing the amount of computation is remarkable as compared to the 400 operations of five-dimensional interpolation. The ray data may be obtained in $\frac{1}{10}$ of the time required for ray tracing by actively utilizing the above-mentioned method. FIG. 13 shows the second PSF obtaining method by summarizing schematically the procedure for obtaining the PSF described in detail above.

Next, parameterization of the PSF will be discussed. A ten-fold increase in computing speed is realized by computing the ray data by means of spline interpolation instead of ray tracing, as described above. However, the required time of three years and 8 months (44 months) is reduced merely to 4.4 months to create a moving picture of one minute in length. In terms of processing time per one frame, 64,000 seconds (17 hours 46 minutes and 40 seconds) has been reduced only to 6,400 seconds (1 hour 46 minutes and 40 seconds). Practically, it is desirable to reduce the processing time per one frame to on the order of several minutes. Because the computation for obtaining the PSF takes the most time in the present method, it is most effective to reduce this computation.

In order to obtain the PSF of the object points $(D_0, \mu_{i0}, v_{i0})$ strictly, a large number of rays must be traced or interpolated to find the density of rays. However, the obtained PSF is a discrete function in unit of pixel and the density is represented by a number of rays per pixel. When the rays are concentrated (in focus), a large amount of rays enter in a small number of pixels and the function is close to a continuous function. However, when the rays are scattered in a wide range (out of focus), the number of rays entering in a unit pixel is small and the error is large. A large amount of additional rays are required in order to cover the function. Then, it is possible to escape from the above-mentioned dilemma by assuming that the PSF is a continuous function from the beginning and by applying its parameters by using the data of ray tracing. Thus, it is not necessary to find parameters for all of the object points and the PSF may be found by spline interpolation (three-dimensional) by selecting only certain sampling points.

What kind of function the distribution function should be will now be discussed. Because most PSFs assume the shape of a peak or mountain (Gaussian distribution), a two-dimensional normal distribution is considered to be adequate. That is, Equation 8

$$p(\mu_o, v_o, u - \mu_o, v - v_o) = p(\mu_o, v_o, s, t)$$
$$= \frac{1}{2\pi\sigma_s\sigma_t\sqrt{1-\rho^2}} \exp\left(-\frac{1}{2(1-\rho^2)}\left(\frac{s^2}{\sigma_s} - 2\rho\frac{st}{\sigma_s\sigma_t} + \frac{t^2}{\sigma_t}\right)\right)$$

$$\sigma_s = \sigma_s(D, \mu_i, v_i)$$

Where, $s = u - \mu_o$, $t = v - v_o$ are deviation from the direction $(\mu_o, v_o)$, and $\sigma_s$, $\sigma_t$ and $\rho$ are parameters of the normal distribution. These parameters have following properties: $-1 < \rho < 1$, $\sigma_s > 0$, $\sigma_t > 0$. The values of these parameters vary with object point $(D_i, \mu_i, v_i)$, i.e. they may be expressed as:

$$\sigma_s = \sigma_s(D_i, \mu_i, v_i)$$

$$\sigma_t = \sigma_t(D_i, \mu_i, v_i)$$

$$\rho = \rho(D_i, \mu_i, v_i)$$

Thus, three-dimensional spline interpolation may be used to minimize the amount of calculation.

In all points (s,t) in an ellipse

Equation 9

$$\frac{1}{2(1-\rho^2)}\left(\frac{s^2}{\sigma_s} - 2\rho\frac{st}{\sigma_s\sigma_t} + \frac{t^2}{\sigma_t}\right) = \frac{c^2}{2}$$

The PSF has the same value

Equation 10

$$p(s, t) = \frac{1}{2\pi\sigma_s\sigma_t\sqrt{1-\rho^2}} \exp\left(-\frac{c^2}{2}\right)$$

Thereafter, integration within its equi-value ellipse turns out as follows:

Equation 11

$$P(c) = \int_S \int p(s,t) ds dt = 1 - \exp\left(-\frac{c^2}{2}\right)$$

Figure 17:
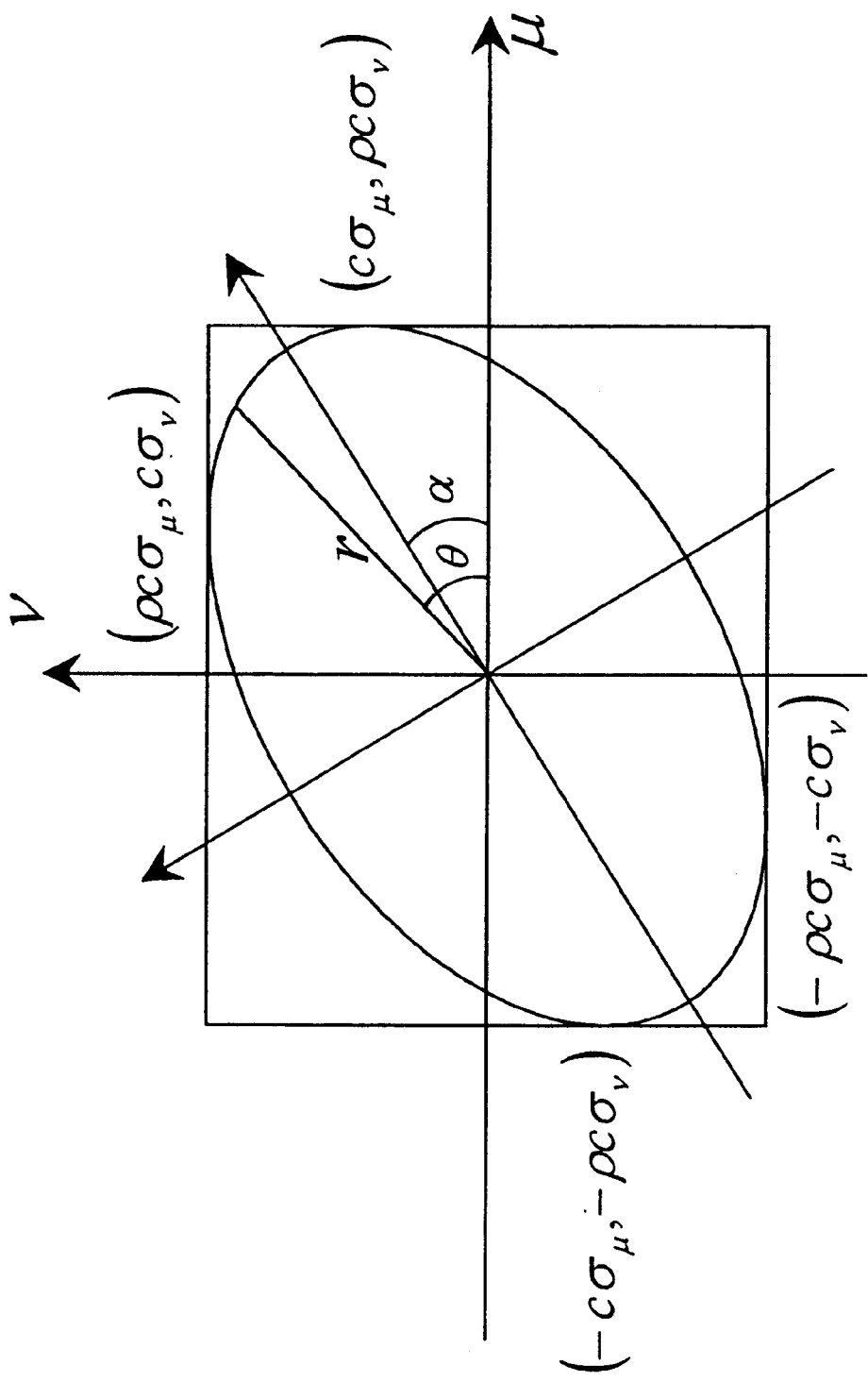
FIG. 17 is a graph showing an equi-probability ellipse.

The shape of the equi-value ellipse is determined by the shape of a circumscribing rectangular $\sigma_s/\sigma_t$ and $\rho$ as shown in FIG. 17 and the size thereof is decided by a number of radiuses c. When the equation of the ellipse is rewritten in polar coordinates, the ellipse turns out as follows:

Equation 12

$$\frac{r^2}{2(1-\rho^2)}\left(\frac{\cos^2\theta}{\sigma_\mu^2} - 2\rho\sin\theta\cos\frac{\theta}{\sigma_\mu\sigma_v} + \frac{\sin^2\theta}{\sigma_v^2}\right) = \frac{1}{2}$$

When it is reduced, it turns out as follows:

Equation 13

$$r^2 = \frac{c^2}{A + B\cos(2\theta - 2\alpha)}$$

Here,

Equation 14

$$A = \frac{1}{2(1-\rho^2)}\left(\frac{1}{\sigma_\mu^2} + \frac{1}{\sigma_v^2}\right)$$

$$B = \frac{1}{2(1-\rho^2)}\sqrt{\left(\frac{1}{\sigma_\mu^2} + \frac{1}{\sigma_v^2}\right)^2 - \frac{4(1-\rho^2)}{\sigma_\mu^2\sigma_v^2}}$$

-continued $$\tan 2\alpha = \frac{2\rho\sigma_\mu\sigma_v}{\sigma_\mu^2 - \sigma_v^2}$$

Because A>thus B holds steadily, the maximum and minimum values of r, i.e., length of major and minor axes of the ellipse, turn out as follows:

Equation 15

$$r_{max}^2 = \frac{c^2}{A-B}$$

$$r_{min}^2 = \frac{c^2}{A+B}$$

Angles of the major and minor axes are $\alpha$ and $\alpha+\pi/2$. These are important quantities for evaluating direction and degree of astigmatic blur.

Thus, the two-dimensional normal distribution function can show the degree of spread ($\sigma_s,\sigma_t$), the degree of astigmatic blur (ratio of major and minor axes of the equi-value ellipse), and the angle (angle of the major axis). Although it is unable to show changes close to infinity caused by the state of the optical system of the PSF faithfully as a matter of course, the function may be effective as a simplified function for expressing the PSF.

When a method for finding the parameters $\sigma_s$, $\sigma_t$ and $\rho$ of the two-dimensional normal distribution function from the ray data is considered, a method of finding a statistic value of intersections of a large number of rays (each intersection corresponds to each divisional point on the entrance pupil) scattering on the plane ($\mu,v$) and of applying them to $\sigma_s$, $\sigma_t$ and $\rho$ comes up naturally. That is, it turns out as follows:

Equation 16

$$\sigma_{s0} = \sqrt{\frac{1}{N}\sum_j s_j^2}$$

$$\sigma_{t0} = \sqrt{\frac{1}{N}\sum_j t_j^2}$$

$$\rho = \frac{\frac{1}{N}\sum_j s_j t_j}{\sigma_{s0}\sigma_{t0}}$$

Where $s_j$ and $t_j$ are derived from a sample ray, N is the number of sample rays. $\sigma_{s0}$, $\sigma_{t0}$ and $\rho$ are statistic amounts of the distribution to the end and are not adequate in many cases as parameters of an approximate normal distribution, as will be discussed below.

Figure 18:
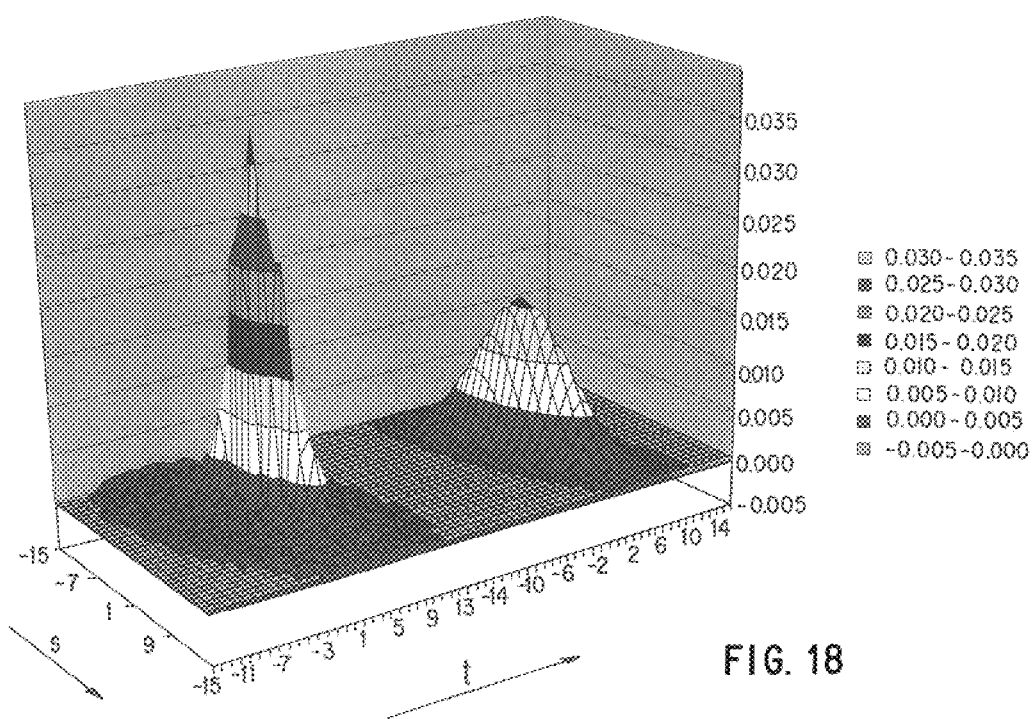
FIG. 18 is a graph showing an actual distribution of density of rays (PSF) and an approximate normal distribution using $\sigma_{s0}$, $\sigma_{t0}$, and $\rho$.
Figure 19:
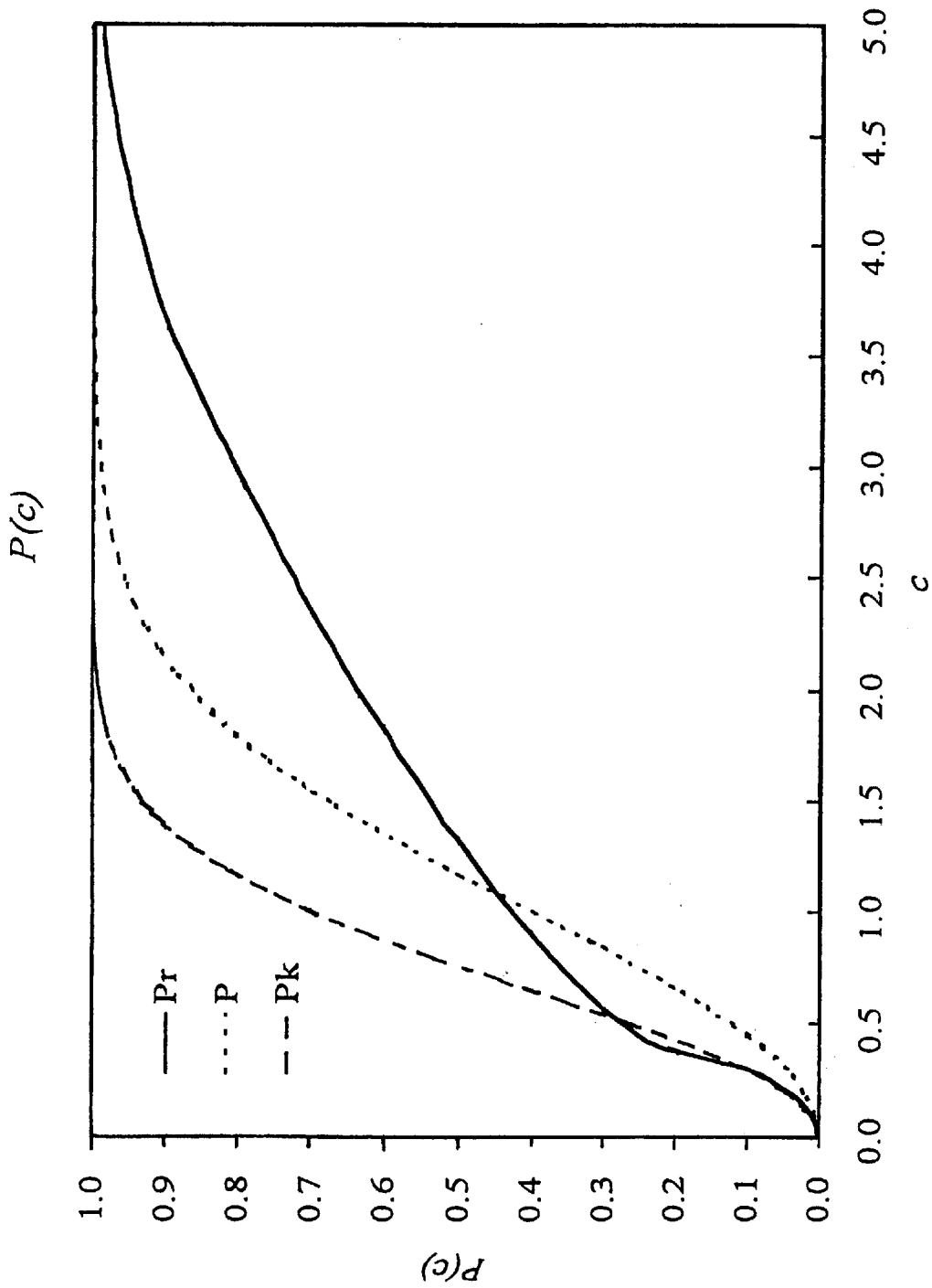
FIG. 19 is a graph showing curves of P(c), $P_k(c)$ and $P_r(c)$.
Figure 20:
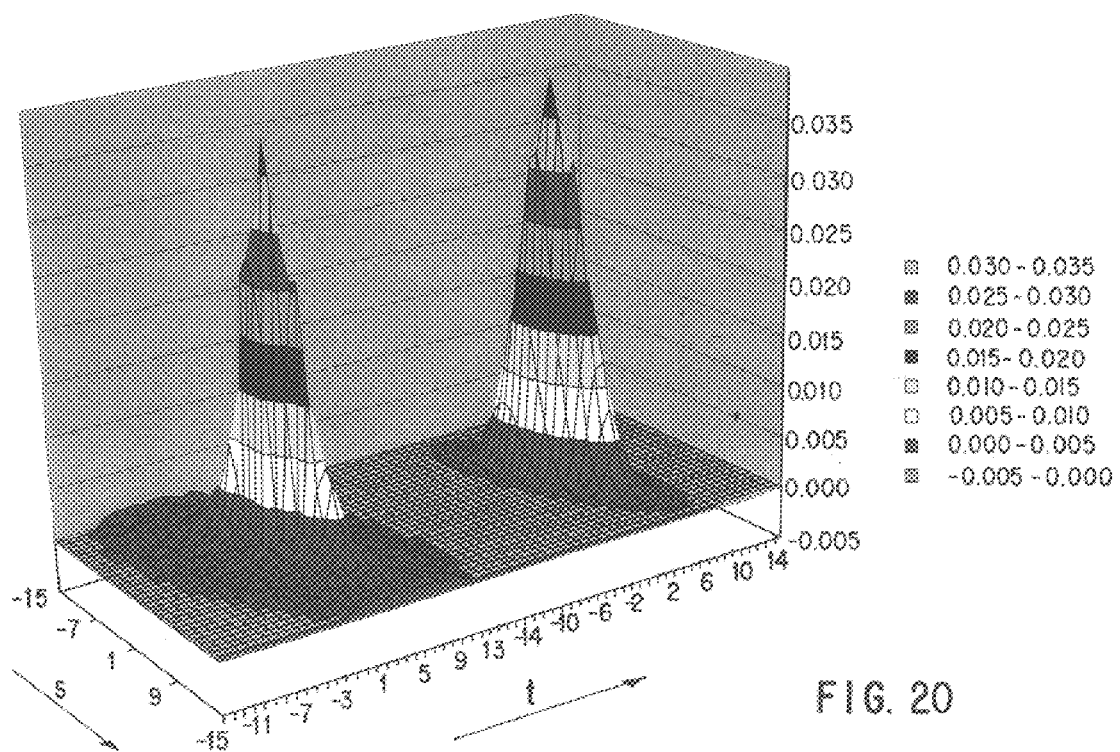
FIG. 20 is a graph showing an actual distribution of density of rays (PSF) and an approximate normal distribution using $k\sigma_{s0}$, $k\sigma_{t0}$, and $\rho$.

FIGS. 18, 19 and 20 illustrate a method of determining parameters of a 2-dimensional gauss function that mostly approximates the actual PSF. In FIG. 18 and 20, the left peak represents the actual PSF and the right peak represents the approximate gauss function. In FIG. 18, the approximate gauss function directly uses the statistical values of $\sigma_{s0},\sigma_{t0},\sigma$ (equation 16). The figure shows that the two PSFs, the actual and the approximate, are quite different. In FIG. 20, the deviations are amended by a constant k, i.e. the parameters are changed to $k\sigma_{s0},k\sigma_{t0},\sigma$. The figure shows that this approximate gauss function fits the actual PSF quite well. One method of determining the constant k is illustrated in FIG. 19.

In FIG. 18, the left peak indicates the density of intersections of the actual PSF and the right peak indicates the approximate PSF which is the normal distribution parameterized by $\sigma_{s0},\sigma_{t0},\sigma$. The units in FIGS. 18 and 20 are pixels of an image. One pixel equals 0.005 in the figures. The origins in each of the s and t axes are located at the center of each peak.

When the approximate PSF is calculated as the normal distribution directly applying $\sigma_{s0},\sigma_{t0}\sigma$ as shown on the right in FIG. 18, although the direction of the main axis and the ratio between the major and minor axes agree with the actual distribution shown on the left in the figure, the degree of spread is considerably different from the actual distribution.

A considerably closer approximation to the actual distribution of the PSF is obtained by defining an adequate proportional coefficient as follows: $\sigma_s=k\sigma_{s0}$ and $\sigma_t=k\sigma_{t0}$. Thereafter, the question becomes how to decide k. One manner of determining the constant k is by use of the relational curve of a probability P(c) within the equi-value ellipse and number of radiuses c. The function P(c) is the integral of PSF within an ellipse whose scale is expressed by a radius-like value c (equation 9). In another words, P(c) is the percentage of spots within that ellipse to the total number of samples. When c gets bigger, P(c) increases and finally become 1. In FIG. 19, $P_r(c)$ represents that of the actual PSF, P(c) relates to the approximate gauss function whose parameters are $\sigma_{s0},\sigma_{t0},\rho$ and $P_k(c)$ relates to $k\sigma_{s0},k\sigma_{t0},\rho$. Let $P_r(c)$ and $P_k(c)$ have the same percentage $P_0$ at $c=C_r$ where $C_r$ can be calculated from $P_r(c)$, and calculate $C_0$ to satisfy $P(C_o)=P_0$ with equation 11, then the constant k can be easily derived as $$k = \frac{C_r}{C_0}.$$

In this embodiment, $P_0$ is set to 0.1.

As stated above, the P(c) curve of the normal distribution when the parameters have been changed to $\sigma_s=k\sigma_{s0}$, $\sigma_t=k\sigma_{t0}$ and $\rho$ is $P_k(c)=1-\exp(-c^2/2k^2)$. Variable k is then determined so as to bring it closer to the P(c) curve of the actual distribution of the PSF.

FIG. 19 shows plots of the curves of P(c), $P_k(c)$ and $P_r(C)$ in the example of FIG. 18. The center part is important in particular in finding the best approximations of the distribution of the PSF. Accordingly, $P_k(c)$ is preferably as close as possible to the $P_r(c)$ curve when c is small. The curve P(c) when the statistical values $\sigma_{s0}$, $\sigma_{t0}$ and $\rho$ are applied is different from the actual distribution $P_r(c)$ and is inadequate as an approximate distribution function. However, the curve $P_k(c)$ of the normal distribution to which $\sigma_s=k\sigma_{s0}$ and $\sigma_t=k\sigma_{t0}$ and $\rho$ have been applied has parts which more closely coincide with the $P_r(c)$ and is a closer approximation to the actual distribution. FIG. 20 shows a comparison of the actual distribution of the PSF (left peak) and the approximation $\sigma_s=k\sigma_{s0}$, $\sigma_t=k\sigma_{t0}$ and $\rho$ (right peak).

The method of calculating k in the present embodiment will now be reviewed in detail. At first, a value of the probability $P_0$ at the point A where the $P_r(c)$ curve crosses with the P(c) curve is determined. Because the part around the center is stressed, $P_0$ is set at 0.1. At the point $P(c)=P_0$ on the P(c) curve, it turns out as follows:

Equation 17

$$C_0 = \sqrt{2\ln\frac{1}{1-P_0}} = 0.459$$

When the point A on the $P_r(c)$ curve is c=C, $k=C_r/C_0$.

Although other methods of determining k (e.g., minimizing the difference between $P_r(c)$ and $P_k(c)$ around the center) are conceivable, the above-mentioned method is the most simple. Thus, the PSF distribution function of the arbitrary object point $(D_j,u_i,v_i)$ on the object space may be approximated by the two-dimensional normal distribution function having the parameters $\sigma_s$, $\sigma_t$ and $\rho$. Parameters $\sigma_s$, $\sigma_t$ and $\rho$ need not be found with respect to all object points encountering in the process of the simulation as a matter of course. Parameters $\sigma_s$, $\sigma_t$ and $\rho$ may be found by spline interpolation at an arbitrary object point by finding only $\sigma_s$, $\sigma_t$ and $\rho$ on the sampling point in advance. Thereby, considerable computing time may be saved.

Figure 21:
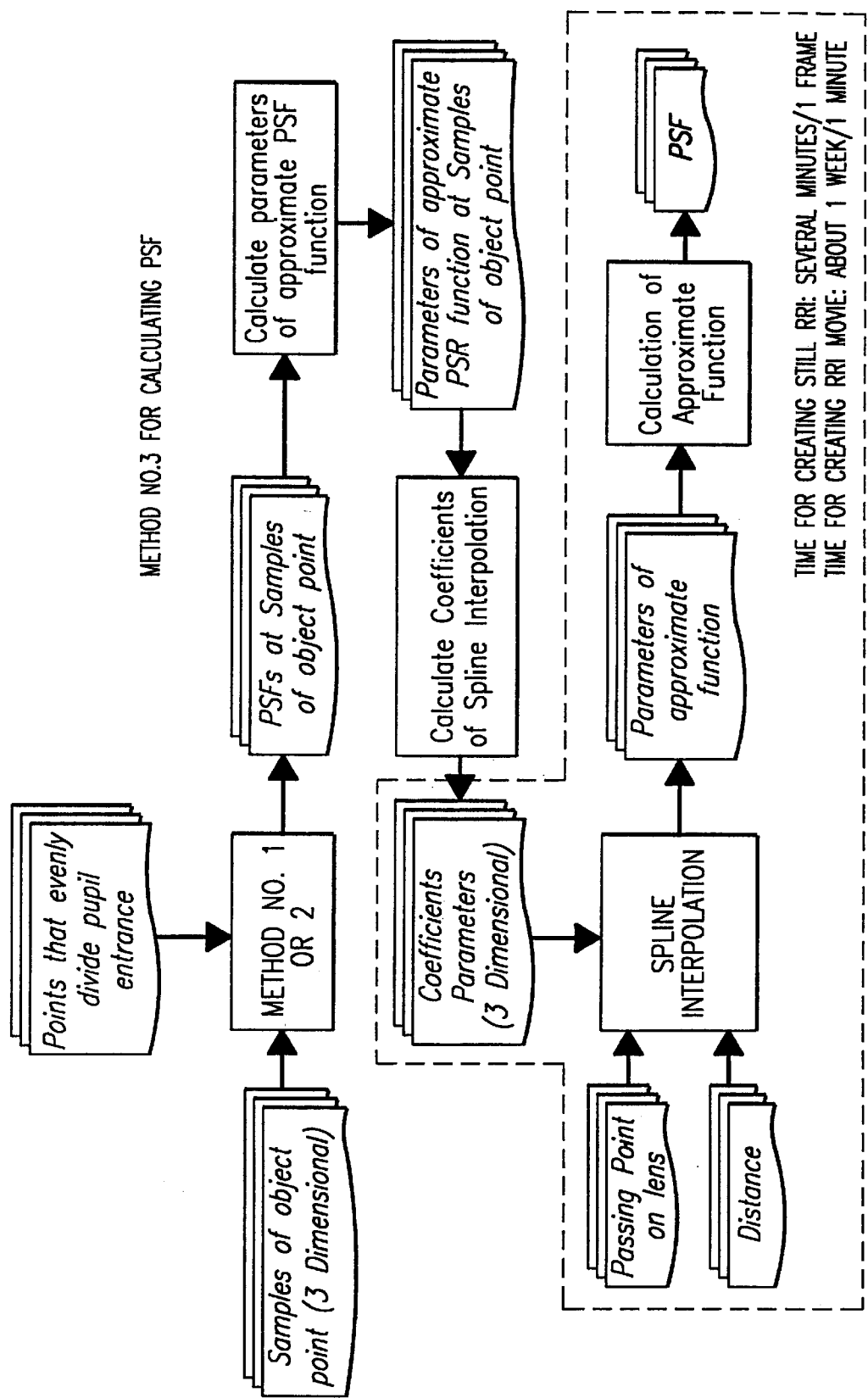
FIG. 21 is a chart showing a third method for obtaining the PSF.

The inventors have succeeded in reducing the processing time per one frame from 1 hour 46 minutes 40 seconds to about 2 to 10 minutes by parameterizing the PSF distribution function. The processing time has some latitude because the processing time changes depending on the degree of blur. It takes about 100 hours, i.e., around one week, to create a moving picture of about one minute. FIG. 21 summarizes the schematic procedure for obtaining the PSF described above in detail as a third PSF obtaining method.

The second embodiment described above enables one to obtain a motion picture image in which fluctuation occurring when the position of the eye is changed or when the line of sight is moved is reproduced in addition to the blur and deformation perceived when seen through a lens system such as a PAL. Accordingly, it becomes possible to evaluate a lens as if one is wearing the lens by displaying the motion image thus obtained on a display unit. The blur, deformation and fluctuation may be seen while confirming the movement of the line of sight on the lens by displaying points where the line of sight passes through the lens on the display screen of the motion image of the rotation-based retinal image.

Figure 22:
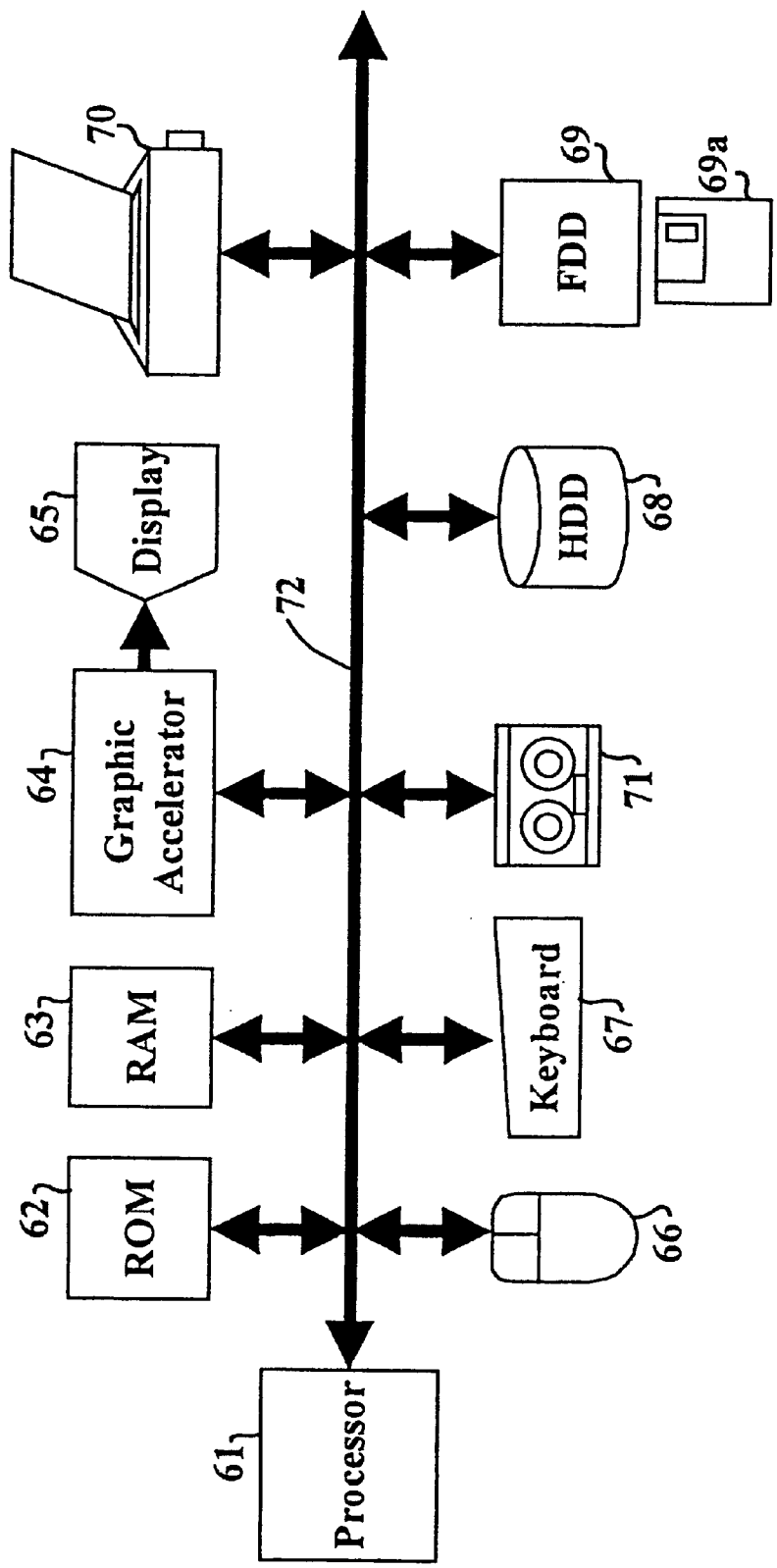
FIG. 22 is a block diagram showing the structure of an apparatus for implementing the ocular optical system simulating method of the present invention.

Next, a system for simulating as described above in the embodiments will be briefly explained. FIG. 22 is a block diagram schematically showing the structure of the system for simulating according to the preferred embodiments. As shown in FIG. 22, the system comprises a processor 61, a read only memory (ROM) 62, a main memory 63, a graphic control circuit 64, a display unit 65, a mouse 66, a keyboard 67, a hard-disk drive (HDD) 68, a floppy disk drive (FDD) 69, a printer 70, a magnetic tape unit 71, etc. These elements are connected by a data bus 72.

The processor 61 controls the whole system. A program necessary in starting is stored in the read only memory 62. A simulation program for performing the simulation is stored in the main memory 63. The graphic control circuit 64 contains a video memory and displays obtained image data on the display unit 65 by transforming them into display signals. The mouse 66 is a pointing device for selecting various icons, menus, etc., on the display unit. A system program, the simulation program, etc., are stored in the hard disk drive 68 and are loaded to the main memory 63 after turning ON. The main memory 63 also stores simulation data temporarily.

The floppy disk drive 69 inputs necessary data such as original image data via a floppy 69a or saves it to the floppy 69a as necessary. The printer 70 is used to print out the retinal image, etc. The magnetic tape unit 71 is used to save simulation data to a magnetic tape as necessary. It is noted that the system having the basic structure described above may be constructed by using a high performance personal computer, or a general-purpose computer.

As described above in detail, the inventive ocular optical system simulating method and simulating apparatus are characterized in that, rather than an optical image projected to the retinal surface of an eye, a rotation-based retinal image is created. The rotation-based image is defined as an image obtained by turning the eye-ball with respect to all object points within a field of vision and by connecting images caught at the fovea. According to the invention, the image is created by computer simulation and represents an image perceived by the eye through a lens system. According to a preferred embodiment, the rotation-based retinal image is created by a method in which an original image creating step creates an image having a specific angular field of vision and entering the eye having a specific rotation center point. A deformed original image creating step creates, by using ray tracing, a deformed original image having deformation occurring when the original image is seen through the lens system. A PSF obtaining step determines the PSF on the retina of an eye-model caused by light from the object points of the original image in an optical system composed of the lens system and a spectacle model. Lastly, a step of convoluting is carried out, in which the deformed original image found in the deformed original image creating step is convoluted with the PSF for each pixel of the original image found in the PSF obtaining step. The thus-obtained rotation-based retinal image is edited further to produce a motion picture image of the rotation-based retinal image. The PSF is determined by selecting sampling points on the object point, and PSF other than those at the sampling points are found by using approximation methods including spline interpolation in the PSF creating step. Thereby, it is possible to obtain an ocular optical system simulating method and simulating apparatus which enables simulation of how things can be seen, together with fluctuation, deformation, blur, etc., occurring when the lens system such as the progressive addition lens (PAL) is worn.

While the present invention has been illustrated by reference to certain Preferred Embodiments and Examples, one of ordinary skill in the art will recognize that modifications, improvements, additions, deletions, and substitutions to the Preferred Embodiments may be made without departing from the spirit and scope of the present invention. The scope of the invention is defined solely by the appended claims.

What is claimed is:

1. A method for simulating an optical system comprising the steps of:
    (1) providing an eye simulation having a central visual line and a center of rotation;
    (2) providing a lens simulation;
    (3) creating a rotation-based optical image within a given field of view centered with said central visual line, comprising turning the eye-simulation with respect to objects in the field of view and connecting images to simulate an image perceived by an eye through the lens simulation.

2. A method according to claim 1, further comprising a step of providing a story of changing position of the center of rotation and direction of the central visual line with time, repeating the step (3) for predetermined points in time to create a static rotation-based retinal image for each point in time, and composing these static rotation-based retinal images into animation.

3. Animation data of rotation-based retinal image obtained by the method of claim 2.

4. A method for simulating an optical system according to claim 1, further comprising the steps of displaying said rotation-based optical image, and indicating a position on said lens simulation through which the images have come.

5. Rotation-based retinal image data obtained by the method of claim 1.

6. A method for simulating how things are seen through a lens system placed in front of the eye, said eye having a retina, a center of rotation placed at a specific position and a central visual line directed to a specific direction, said method comprising the steps of:

(1) creating an original image within a field of view centered about said central visual line;

(2) creating a deformed original image to approximate deformation occurring when the original image is seen through said lens system;

(3) determining point spread functions, defined as a distribution of luminance on the retina originating from a given object point, for each object point within the original image;

(4) convoluting the deformed original image with the point spread functions to create a rotation-based retinal image.

7. A method according to claim 6, wherein said step of creating an original image comprises preparing at least one object within a space, placing said center of rotation at a specific position, directing said central visual line in a specific direction, creating an image of objects inside said field of view, and measuring distances from the object within said field of view to the center of rotation;

wherein said step of creating a deformed original image comprises determining a position on said lens system through which the object is observed, tracing a principal ray that emits from each of a plurality of object points within the field of view and passes through a position on said lens system and heads towards the center of rotation, calculating relative positions of the object points in an after-lens field of view from directions of principal rays output from said lens system, and creating a deformed original image that represents the relative positions of the object points in an after-lens field of view;

wherein said step of determining the point spread function related to each object point comprises turning the eye to view that object point, adjusting the eye to an accommodation power that most appropriate to view that object point, and calculating a point spread function with the optical system combined with the lens system and the eye;

wherein said step of convoluting comprises convoluting the deformed original image with the point spread function determined for each object point to produce a rotation-based retinal image.

8. A method according to claim 7, further comprising a step of providing a story that describes (1) positions of the eye, (2) orientations of the eye and (3) positions on the lens system through which the field of view is observed for predetermined points in time, creating static deformed original images and static rotation-based retinal images for each point in time and composing these static deformed original images and rotation-based retinal images into animation.

9. Animation data of rotation-based retinal image and deformed original image obtained by the method of claim 8.

10. A method for simulating an optical system according to claim 7, further comprising the steps of displaying said rotation-based optical image, and indicating a position on said lens simulation through which the images have come.

11. Rotation-based retinal image data and deformed original image data obtained by the method of claim 7.

12. A method according to claim 6, wherein said step of creating an original image comprises (1) creating at least one virtual object and placing the object in a virtual three-dimensional space by computer graphics, determining the position of the center of rotation and the direction of the central visual line of the eye in the three-dimensional space;

(2) capturing the image of the objects within a field of view whose central direction is placed at said central visual line of the eye; and (3) measuring the distance from each of a plurality of object points in the field of view to the center of rotation.

13. A method according to claim 6, wherein said step of creating a deformed original image comprises (1) determining a passing point that indicates a position on the lens system through which the field of view is observed, (2) tracing to find a principal ray that emits from an object point at the center of the field of view and passes through the passing point and heads towards the center of rotation, (3) defining an after-lens field of view whose central direction is identical to the output direction from the lens system of the central principal ray, (4) tracing to find a principal ray that emits from each of a plurality of object points related to each pixel of the original image and passes through the lens system and head towards the center of rotation, to thereby obtain the positions of the object points in the after-lens field of view and passing points where the principal rays pass through the lens system.

14. A method according to claim 13, wherein said step of creating a deformed original image, calculating the positions in the after-lens field of view of each of a plurality of object points and determining passing points on the lens system for each object point in the field of view is accomplished by spline interpolation instead of tracing every ray.

15. A method according to claim 13, wherein said step of creating a deformed original image, obtaining positions in the after-lens field of view and determining passing points on the lens system is accomplished with the following functions:

$\mu_0 = \mu_0(D, u_i, v_i)$,
$v_0 = v_0(d, u_i, v_i)$,
$y_s = y_s(D, u_i, v_i)$,
$z_s = z_s(D, u_i, v_i)$, where $\mu_0$ and $v_0$ indicate the position in the after-lens field of view, $y_s$ and $z_s$ indicate the passing point on the lens system, $D, u_i, v_i$ indicate the object point in the original field of view that satisfy $D = 1/\sqrt{x^2+y^2+z^2}$, $u_i = y/x$, $v_i = z/x$; and each of the above functions is approximated by a three-dimensional spline expression:

$$F = F(D, \mu_i, v_i) = \sum_l \sum_m \sum_n C_{l,m,n} N_m(D) N_n(\mu_i) N_l(v_i),$$

in which coefficients $C_{i,m,n}$ are determined by tracing rays for a finite number of sample object points selected appropriately to obtain values of F and fitting these values into the three-dimensional spline expression.

16. A method according to claim 6, wherein said step of determining the point spread function for each object point comprises (1) determining power of accommodation of the eye according to (a) a distance between the object point and the center of rotation, (b) a refractive power of the lens system at the passing point of the principal ray from said object point and (c) a capacity of accommodation, (2) setting a finite number of points that evenly distribute on an entrance pupil of the eye, tracing rays emitting from the object point and pass through these points in the optical system combined with the lens system and the accommodated eye turned to view the object point, (3) calculating one of (a) the distribution of density of spots on the retina as the point spread function or (b) the distribution of light intensity as the point spread function by diffractive integration, (4) transforming the point spread function as a function of position on the retina to a point spread function as a function of position in the after-lens field of view according to Listing's law.

17. A method according to claim 16,
wherein said step of determining the point spread function, is accomplished by calculating point spread functions for each object point in the field of view by spline interpolation.

18. A method according to claim 16,
wherein said step of determining the point spread functions, the spot on retina and, if necessary, the optical path length of an element optical ray, is accomplished with the following functions:

$y_m = y_{mpl}(D, \mu_i, v_i, y_p, z_p)$, $z_m = z_m(D, \mu_i, v_i, y_p, z_p)$, where $y_m$ and $z_m$ indicate the spot on the fovea, $D, \mu_i, v_i$ indicate an object point in the original field of view, and $y_p, z_p$ indicate the passing point on the entrance pupil; and wherein each of the above functions is approximated as a five-dimensional spline expression:

$$F = F(D, \mu_i, v_i, y_p, z_p)$$
$$= \sum_j \sum_k \sum_l \sum_m \sum_n C_{j,k,l,m,n} N_m(D) N_n(\mu_i) N_l(v_i) N_k(y_p) N_j(z_p),$$

in which coefficients $C_{j,k,l,m,n}$ are determined by tracing rays for a finite number of sample object points and passing points on the entrance pupil selected appropriately to obtain values of F and fitting these values into the spline expression.

19. A method according to claim 16,
wherein, in said step of determining the point spread function, the point spread function of each object point is expressed as and calculated with a parameterized function of position on the retina or transformed position in the after-lens field of view, each parameter is a function of an object point and expressed with a three-dimensional spline interpolation.

20. A method according to claim 16,
wherein said step of determining the point spread function, p(s,t) of each object point is calculated with a two-dimensional normal distribution parameterized with $\sigma_s$, $\sigma_t$ and $\rho$, wherein:

$$p(s,t) = \frac{1}{2\pi\sigma_s\sigma_t\sqrt{1-\rho^2}} \exp\left(-\frac{1}{2(1-\rho^2)}\left(\frac{s^2}{\sigma_s^2} - 2\rho\frac{st}{\sigma_s\sigma_t} + \frac{t^2}{\sigma_t^2}\right)\right)$$

wherein s and t are deviations from the principal ray in the vertical and horizontal directions within the after-lens field of view, and each of $\sigma_s$, $\sigma_t$ and $\rho$ is calculated with a three-dimensional spline expression:

$$F = F(D, \mu_i, v_i) = \sum_l \sum_m \sum_n C_{l,m,n} N_m(D) N_n(\mu_i) N_l(v_i),$$

in which coefficients $C_{l,m,n}$ are determined by calculating values of F for a finite number of appropriate sample object points and fitting these values into the three dimensional spline expression.

21. A method according to claim 6, further comprising a step of providing a story that describes (1) positions of the eye, (2) orientations of the eye and (3) positions on the lens system through which the field of view is observed for predetermined points in time, creating static deformed original images and rotation-based retinal images for each point in time and composing these static deformed original images and rotation-based retinal images into animation.

22. Animation data of rotation-based retinal image and deformed original image obtained by the method of claim 21.

23. A method for simulating an optical system according to claim 6, further comprising the steps of displaying said rotation-based optical image, and indicating a position on said lens simulation through which the images have come.

24. Rotation-based retinal image data and deformed original image data obtained by the method of claim 6.

25. An apparatus for simulating an optical system comprising:

(1) an eye simulation having a central visual line and a center of rotation;

(2) a lens simulation; and (3) a computer having (a) a memory with a graphics image containing objects stored therein, (b) processor means for creating a rotation-based optical image within a given field of view, by turning the eye-simulation with respect to an object in the field of view and connecting images to simulate an image perceived by an eye through the lens simulation, and (c) means for displaying the rotation based optical image.

26. An apparatus according to claim 25, further comprising means for providing a story of changing position of the center of rotation and direction of the central visual line with time, repeating the step of creating a static rotation-based retinal image for each point in time, and composing these static rotation-based retinal images into animation.

27. An apparatus according to claim 25, further comprising means for displaying said rotation-based optical image, and indicating a position on said lens simulation through which the images have come.

28. An apparatus for simulating how things are seen through a lens system placed in front of an eye, said eye having a center of rotation placed at a specific position and a central visual line directed to a specific direction, said apparatus comprising:

(1) means for creating an original image within a field of view centered about said central visual line;

(2) means for creating a deformed original image to approximate deformation occurring when the original image is seen through said lens system;

(3) means for determining point spread functions, defined as a distribution of luminance on the retina originating from a given object point, for each object point within the original image;

(4) means for convoluting the deformed original image with the point spread functions to create a rotation-based retinal image; and (5) means for displaying the rotation based retinal image.

29. An apparatus according to claim 28, wherein said means for creating an original image comprises preparing an object within a space, placing said center of rotation at a specific position, directing said central visual line in a specific direction, creating an image of the object inside said field of view, and measuring distances from the object within said field of view to the center of rotation;

wherein said means for creating a deformed original image comprises determining a position on said lens system through which the object is observed, tracing a principal ray that emits from each of a plurality of object points within the field of view and passes through the position on said lens system and heads towards the center of rotation, calculating relative positions of the object points in an after-lens field of view from directions of the principal rays output from said lens system, and creating a deformed original image that represents the relative positions of the object points in an after-lens field of view;

wherein said means for determining the point spread function related to each object point comprises turning the eye to view that object, adjusting the eye to an accommodation power most appropriate to view that object point, and calculating a point spread function with the optical system combined with the lens system and the eye;

wherein said means for convoluting comprises convoluting the deformed original image with the point spread function determined for each object point to produce the rotation-based retinal image.

30. An apparatus according to claim 29, further comprising means for providing a story that describes (1) positions of the eye, (2) orientations of the eye and (3) positions on the lens system through which the field of view is observed for predetermined points in time, creating deformed original images and rotation-based retinal images for each point in time and composing these static deformed original images and rotation-based retinal images into animation.

31. An apparatus according to claim 29, further comprising means for displaying said rotation-based optical image, and indicating a position on said lens simulation through which the images have come.

32. An apparatus according to claim 28, wherein said means for creating an original image comprises means for (1) creating at least one virtual object and placing the object in a virtual three-dimension space by computer graphics, determining the position of the center of rotation and the orientation of the eye in the three-dimension space, (2) capturing the image of the objects within a field of view whose central direction is placed at the said orientation of the eye, and (3) measuring the distance from each of a plurality of object points of the object in the field of view to the center of rotation.

33. An apparatus according to claim 28, wherein the means for creating a deformed original image comprises means for (1) determining a passing point that indicates a position on the lens system through which the field of view is observed, (2) tracing to find a principal ray that emits from the object point at the center of the field of view and passes through the passing point and heads towards the center of rotation, (3) defining an after-lens field of view whose central direction is identical to the output direction from the lens system of the central principal ray, (4) tracing to find principal rays that emit from each of a plurality of object points related to each pixel of the original image and pass through the lens system and head towards the center of rotation, to thereby obtain the positions of the object points in the after-lens field of view and passing points where the principal rays pass through the lens system.

34. An apparatus according to claim 33, wherein said means for creating a deformed original image, obtaining the positions in the after-lens field of view for each of a plurality of object points and determining passing points on the lens system for each object point in the field of view accomplishes these functions by spline interpolation instead of tracing every ray.

35. An apparatus according to claim 33, wherein said means for creating a deformed original image, obtaining the positions in the after-lens field of view and determining the passing points on the lens system accomplishes these steps with the following functions:

$\mu_0 = \mu_0(D, \mu_i, v_i)$, $v_0 = v_0(D, \mu_i, v_i)$ $y_s = y_s(D, \mu_i, v_i)$ $z_s = z_s(D, \mu_i, v_i)$ where $\mu_0$ and $v_0$ indicate the position in the after-lens field of view, $y_s$ and $z_s$ indicate the passing point on the lens system, $D, \mu_i, v_i$ indicate the object point in the original field of view that satisfy $$D = 1/\sqrt{x^2+y^2+z^2},\ \mu_i = y/x,\ v_i = z/x$$

wherein each of the above functions is approximated as a three-dimensional spline expression:

$$F = F(D, \mu_i, v_i) = \sum_l \sum_m \sum_n C_{l,m,n} N_m(D) N_n(\mu_i) N_l(v_i),$$

in which coefficients $C_{l,m,n}$ are determined by tracing rays for a finite number of sample object points and passing points on the entrance pupil selected appropriately to obtain values of F and fitting these values into the spline expression.

36. An apparatus according to claim 28,
wherein the means for determining the point spread function for each object point comprises means for
(1) determining power of accommodation of the eye according to
(a) a distance between the object point and the center of rotation,
(b) a refractive power of the lens system at the passing point of the principal ray from said object point and
(c) a capacity of accommodation,
(2) setting a finite number of points that evenly distribute on an entrance pupil of the eye, tracing rays emitting from the object point and passing through the points in the optical system combined with the lens system and the accommodated eye turned to view the object point,
(3) calculating one of (a) the distribution of density of spots on the retina as the point spread function or (b) the distribution of light intensity as the point spread function by diffractive integration,
(4) transforming the point spread function as function of position on the retina to a point spread function as a function of position in the after-lens field of view according to Listing's law.

37. An apparatus according to claim 36,
wherein said means for determining the point spread function, determines the point spread functions for each object point in the field of view by spline interpolation.

38. An apparatus according to claim 36,
wherein said means for determining the point spread functions, determines the point spread function, the spot on retina and, if necessary, the optical path length of an element optical ray, with the following functions:
$y_m = y_m(D, u_i, v_i, y_p, z_p)$,
$z_m = z_m(D, u_i, v_i, y_p, z_p)$,
where $y_m$ and $z_m$ indicate the spot on retina, $D, u_i, v_i$ indicate the object point in the original field of view, and $y_p, z_p$ indicate the passing point on the entrance pupil; and
each of the above functions is approximated as a five-dimensional spline expression:

$$F = F(D, \mu_i, v_i, y_p, z_p)$$
$$= \sum_j \sum_k \sum_l \sum_m \sum_n C_{j,k,l,m,n} N_m(D) N_n(\mu_i) N_l(v_i) N_k(y_p) N_j(z_p),$$

in which coefficients $C_{j,k,l,m,n}$ are determined by tracing rays for a finite number of sample object points and passing points on the entrance pupil selected appropriately to obtain values of F and fitting these values into the spline expression.

39. An apparatus according to claim 36,
wherein, in said means for determining the point spread functions, the point spread function of each object point is expressed as and calculated with a parameterized function of a position on the retina or a transformed position in the after-lens field of view, each parameter is a function of an object point and expressed with a three-dimensional spline interpolation.

40. An apparatus according to claim 36,
wherein said means for determining the point spread function, p(s,t) of each object point is calculated with a two-dimensional normal distribution parameterized with $\sigma_s$, $\sigma_t$ and $\rho$, wherein:

$$p(s, t) = \frac{1}{2\pi\sigma_s\sigma_t\sqrt{1-\rho^2}} \exp\left(-\frac{1}{2(1-\rho^2)}\left(\frac{s^2}{\sigma_s^2} - 2\rho\frac{st}{\sigma_s\sigma_t} + \frac{t^2}{\sigma_t^2}\right)\right)$$

wherein s and t are deviations from the principal ray in the vertical and horizontal directions within the after-lens field of view, and each of $\sigma_s$, $\sigma_t$ and $\rho$ is calculated with a three-dimensional spline expression:

$$F = F(D, \mu_i, v_i) = \sum_l \sum_m \sum_n C_{l,m,n} N_m(D) N_n(\mu_i) N_l(v_i),$$

in which coefficients $C_{l,m,n}$ are determined by calculating values of F for a finite number of appropriately selected sample object points and fitting these values into the spline expression.

41. An apparatus according to claim 28, further comprising means for providing a story that describes
(1) positions of the eye,
(2) orientations of the eye and
(3) positions on the lens system through which the field of view is observed
for predetermined points in time, creating deformed original images and rotation-based retinal images for each point in time and composing these static deformed original images and rotation-based retinal images into animation.

42. An apparatus according to claim 28, further comprising means for displaying said rotation-based optical image, and indicating a position on said lens simulation through which the images have come.

* * * * *